United States Patent
Helman et al.

(10) Patent No.: US 10,689,674 B2
(45) Date of Patent: *Jun. 23, 2020

(54) SYNTHETIC METHANOTROPHIC AND METHYLOTROPHIC MICROORGANISM AND METHOD THEREOF

(71) Applicant: INDUSTRIAL MICROBES, INC., Emeryville, CA (US)

(72) Inventors: Noah Helman, El Cerrito, CA (US); Elizabeth Clarke, San Francisco, CA (US); Derek Greenfield, Kensington, CA (US)

(73) Assignee: INDUSTRIAL MICROBES, INC., Alameda, CA (US)

( * ) Notice: Subject to any disclaimer, the term of this patent is extended or adjusted under 35 U.S.C. 154(b) by 37 days.

This patent is subject to a terminal disclaimer.

(21) Appl. No.: 15/303,518

(22) PCT Filed: Apr. 14, 2015

(86) PCT No.: PCT/US2015/025817
§ 371 (c)(1),
(2) Date: Oct. 11, 2016

(87) PCT Pub. No.: WO2015/160848
PCT Pub. Date: Oct. 22, 2015

(65) Prior Publication Data
US 2017/0037438 A1 Feb. 9, 2017

Related U.S. Application Data

(60) Provisional application No. 61/979,512, filed on Apr. 15, 2014.

(51) Int. Cl.
C12P 7/46 (2006.01)
C12N 9/04 (2006.01)
(Continued)

(52) U.S. Cl.
CPC .............. C12P 7/46 (2013.01); C12N 9/0006 (2013.01); C12N 9/0008 (2013.01);
(Continued)

(58) Field of Classification Search
CPC .. C12N 9/0006; C12N 9/0071; C12N 9/0077; C12N 15/52; C12N 9/88; C12N 9/0042; C12N 1/20; C12N 9/1022; C12N 9/1025; C12N 9/0073; C12N 15/74; C12N 9/93; C12N 9/0008; C12N 9/0069; C12N 9/16; C12N 15/1058; C12N 15/70; C12N 9/0026; C12N 9/1205; C12N 9/90; C12N 15/00; C12N 15/09; C12N 9/0014; C12N 9/0051; C12N 9/14; C12N 15/63; C12N 15/86; C12N 15/1068; C12N 15/1089; C12N 15/1137; C12N 15/62; C12N 15/635; C12N 2740/16043; C12N 2750/14143; C12N 9/0004; C12N 9/10; C12N 9/1096; C12N 1/36; C12N 15/1065; C12N 15/1079; C12N 15/1082; C12N 15/1086; C12N 15/1093; C12N 1/00; C12N 9/1007; C12P 7/04; C12P 7/06; C12P 7/16; C12P 21/02; C12P 5/023; C12P 13/04; C12P 3/00; C12P 7/24; C12P 7/42; C12P 7/44; C12P 7/64; C12P 7/6409; C12P 7/6436; C12P 17/02; C12P 5/026; C12P 7/22; C12P 7/46; C12P 7/6463; C12P 7/40; C12P 5/00; C12P 7/00; C12P 7/10; C12P 19/02; C12P 7/649; C12Y 114/15003; C12Y 101/01001; C12Y 106/02004; C12Y 114/14001; C12Y 114/15; C12Y 101/01004; C12Y 101/01086; C12Y 202/01006; C12Y 203/03006; C12Y 401/01072; C12Y 402/01009; C12Y 402/01033; C12Y 403/01019; C12Y 114/13025; C12Y 101/01; C12Y 101/01008; C12Y 101/01027; C12Y 102/99006; C12Y 207/0103; C12Y 301/02;
(Continued)

(56) References Cited

U.S. PATENT DOCUMENTS 9,267,158 B2 * 2/2016 Coleman ................... C12P 7/16
9,399,783 B2 * 7/2016 Coleman ................... C12P 7/16
(Continued)

FOREIGN PATENT DOCUMENTS

EP 1433856 6/2004
WO 2013110797 A1 8/2013
(Continued)

OTHER PUBLICATIONS

Jahng et al. (Applied and Environmental Microbiology, Jul. 1994. p. 2473-2482, vol. 60. No. 7).*
(Continued)

*Primary Examiner* — Deborah K Ware
(74) *Attorney, Agent, or Firm* — Squire Patton Boggs (US) LLP

(57) ABSTRACT

Provided herein are non-naturally occurring microbial organisms comprising a methane-oxidizing metabolic pathway. The invention additionally comprises non-naturally occurring microbial organisms comprising pathways for the production of chemicals. The invention additionally provides methods for using said organisms for the production of chemicals.

5 Claims, 3 Drawing Sheets

(51) Int. Cl.
| | |
|---|---|
| *C12N 9/02* | (2006.01) |
| *C12N 9/10* | (2006.01) |
| *C12N 9/88* | (2006.01) |
| *C12N 9/90* | (2006.01) |
| *C12N 9/06* | (2006.01) |

(52) U.S. Cl.
CPC ......... *C12N 9/0014* (2013.01); *C12N 9/1022* (2013.01); *C12N 9/88* (2013.01); *C12N 9/90* (2013.01); *C12Y 101/01001* (2013.01); *C12Y 101/01224* (2013.01); *C12Y 101/02007* (2013.01); *C12Y 101/03013* (2013.01); *C12Y 101/99037* (2013.01); *C12Y 102/01002* (2013.01); *C12Y 102/01046* (2013.01); *C12Y 111/01006* (2013.01); *C12Y 114/13025* (2013.01); *C12Y 202/01003* (2013.01); *C12Y 401/01043* (2013.01); *C12Y 503/01027* (2013.01)

(58) Field of Classification Search
CPC .......... C12Y 503/01027; C12Y 602/01; C12Y 602/01001; C12Y 101/01224; C12Y 101/01244; C12Y 101/02007; C12Y 101/03013; C12Y 101/99037; C12Y 102/01002; C12Y 102/01046; C12Y 111/01006; C12Y 114/00; C12Y 114/18003; C12Y 202/01003; C12Y 308/01005; C12Y 401/01043; C12Y 401/02043; C12Y 101/05006; C12Y 108/05004; C12Y 206/01021; Y02E 50/17; Y02E 50/10; Y02E 50/343; Y02E 50/16; Y02E 50/13; C07K 14/32; C07K 14/195; C07K 14/21; C07K 14/47; C07K 14/4702; Y02P 20/52; Y02P 20/582; Y02P 30/20; Y02P 60/247; B01D 2251/95; B01D 53/84; B01D 2255/804; B01D 2256/24; B01D 2256/245; B01D 2257/2066; B01D 2257/304; B01D 2258/05; B01D 53/70; B01D 53/85; C09K 8/582; C12R 1/01; C12R 1/10; E21B 43/006; B82Y 40/00; C02F 1/683; C02F 1/72; C02F 2101/10; C02F 2101/20; C02F 2101/22; C02F 3/341; C02F 2101/36; C02F 3/34; C07D 413/12; C12Q 1/689; C12Q 1/68; C12Q 1/6853; C12Q 1/686; C12Q 2531/113; C12Q 2561/113; C12Q 2600/16; C12Q 1/6876; C12Q 1/6883; C12Q 2600/142; C12Q 2600/158; C12Q 1/02; C12Q 2600/136; C40B 10/00; C40B 40/08; C40B 50/04; C40B 50/06; A23K 10/10; A23N 17/00; C10G 2300/1025; C10G 2300/202; C10G 2400/02; C10G 2400/04; C10G 2400/08; C10G 3/00; C10L 1/04; C10L 1/06; C10L 1/08; C10L 2290/544; C10L 3/102; Y02A 50/2359; A01N 63/00; A01N 63/02; A01N 63/04; A61K 38/00; A61K 35/74; A61K 35/744; A61K 35/745; A61K 35/747; A61K 48/00; A61K 8/99; A61K 9/0014; A21D 8/042; D06L 4/40; D06M 16/003; G01N 33/573; Y02T 50/678; G16B 25/00; Y10S 707/99945; Y10S 707/99948; A01C 1/06; A01G 22/20; A01G 22/40; A01G 7/00; A61L 15/36; A61Q 15/00; A61Q 17/04; A61Q 19/00; A61Q 19/02; A61Q 19/04
See application file for complete search history.

(56) References Cited

U.S. PATENT DOCUMENTS

| | | | | |
|---|---|---|---|---|
| 9,745,603 | B2* | 8/2017 | Coleman | C12P 7/16 |
| 2005/0176121 | A1* | 8/2005 | Takeshita | C12P 7/04 435/155 |
| 2006/0051782 | A1 | 3/2006 | Wood et al. | |
| 2010/0257778 | A1 | 10/2010 | Gaertner et al. | |
| 2011/0097769 | A1 | 4/2011 | Del Cardayre et al. | |
| 2014/0013658 | A1 | 1/2014 | Silverman et al. | |
| 2014/0162327 | A1 | 6/2014 | Sun et al. | |
| 2014/0273128 | A1* | 9/2014 | Coleman | C12P 7/16 435/160 |
| 2015/0104854 | A1* | 4/2015 | Singh | C12N 9/0071 435/257.2 |
| 2016/0160243 | A1* | 6/2016 | Coleman | C12P 7/16 435/252.3 |
| 2016/0333359 | A1* | 11/2016 | Song | C12N 15/70 |
| 2017/0037438 | A1* | 2/2017 | Helman | C12N 9/0006 |
| 2017/0152529 | A1* | 6/2017 | Coleman | C12P 7/16 |
| 2017/0183638 | A1* | 6/2017 | Jung | C12N 9/0073 |
| 2017/0335351 | A1* | 11/2017 | Coleman | C12P 7/16 |
| 2019/0032028 | A1* | 1/2019 | Clark | C12N 9/0073 |

FOREIGN PATENT DOCUMENTS

| | | |
|---|---|---|
| WO | 2014047209 A1 | 3/2014 |
| WO | WO 2015/013295 | 1/2015 |
| WO | WO 2015/160848 | 10/2015 |

OTHER PUBLICATIONS

Cetinbas et al., (2013) PLoS Connput. Biol. 9(11), pp. 1-11.*
Gou et al., FEMS Microbiol Lett 263 (2006) 136-141.*
West et al., J Gen Microbiol. Jul. 1992;138(7):1301-7.*
Fenton et al, "GroEL-mediated protein folding", Protein Sci. (1997), 6:743-760. (Year: 1997).*
International Search Report issued in PCT/US2015/025817 dated Jul. 21, 2015 (4 pages).
Written Opinion issued in PCT/US2015/025817 dated Jul. 21, 2015 (8 pages).
Smith et al., "Metal reconstitution of particulate methane monooxygenase and heterologous expression of the pmoB subunit", Methods Enzymol. 2011;495:195-210. doi: 10.1016/B978-0-12-386905-0.00013-9.
Blazyk, Jessica L, "Electron Transfer and Protein Engineer Studies of the Soluble Methane Monooxygenase from Methylococus capsulatus (Bath)", Submitted to the Dept. of Chemistry in Partial Fulfillment of the Requirements for the Degree of Doctor of Philosophy in Chemistry at the Massachusetts Institute of Technology, Sep. 2003 (312 pages).
Nguyen et al., "Reconstruction of Methanol and Formate Metabolic Pathway in Non-native Host for Biosynthesis of Chemicals and Biofuels", Biotechnology and Bioprocess Engineering 21: 477-482 (2016), DOI 10.1007/s12257-016-0301-7.
Palmer, Michael A., "Optimization of Growth Conditions for Methanol Consumption in *Escherichia coli* Expressing Methylotrophic Genes", A thesis submitted to the Faculty of the University of Delaware in partial fulfillment of the requirements for the degree of Honors Degree in Chemical Engineering with Distinction, Spring 2016 (41 pages).
Whitaker et al., "Synthetic methylotrophy: engineering the production of biofuels and chemicals based on the biology of aerobic methanol utilization", Current Opinion in Biotechnology 2015, 33:165-175.
Witthoff et al., "Metabolic Engineering of Corynebacterium glutamicum for Methanol Metabolism", Appl Environ Microbiol 81:2215-2225. doi:10.1128/AEM.03110-14.

(56) References Cited

OTHER PUBLICATIONS

"Information on EC 1.14.13.25—methane monooxygenase (soluble)". BRENDA [online database]. Jan. 2018, [retrieved on Jan. 16, 2019]. Retreived from the Internet: URL <https://www.brenda-enzymes.org/enzyme.php?ecno=1.14.13.25>, 12 pages.

Ali et al., "Development and validation of promoter-probe vectors for the study of methane monooxygenase gene expression in *Methylococcus capsulatus* Bath", Microbiology. Mar. 2009; 155(Pt 3): 761-771.

Altschul et al., "Basic Local Alignment Search Tool", J Mol Biol. Oct. 5, 1990; 215(3): 403-410.

Amann et al., "Tightly regulated tac promoter vectors useful for the expression of unfused and fused proteins in *Escherichia coli*", Gene. Sep. 30, 1988; 69(2): 301-315.

Annaluru et al., "Total Synthesis of a Functional Designer Eukaryotic Chromosome", Science. Apr. 4, 2014; 344(6179): 55-58. Epub Mar. 27, 2014.

Antoine et al., "Cloning and over-expression in *Escherichia coli* of the gene encoding NADPH group III alcohol dehydrogenase from *Thermococcus hydrothermalis*. Characterization and comparison of the native and the recombinant enzymes", Eur J Biochem. Sep. 1999; 264(3): 880-889.

Araya-Garay et al., "Construction of a novel Pichia pastoris strain for production of xanthophylls", AMB Express. Apr. 25, 2012; 2(1): 24.

Ausu Bel et al. *Current Protocols in Molecular Biology*. New York, John Wiley & Sons Inc., 2012.

Baik et al., "Mechanistic Studies on the Hydroxylation of Methane by Methane Monooxygenase", Chem Rev. Jun. 2003; 103(6): 2385-2419.

Balasubramanian et al., "Oxidation of methane by a biological dicopper centre", Nature. May 6, 2010; 465(7294): 115-119. Epub Apr. 21, 2010.

Beaucage et al., "Recent Advances in the Chemical Synthesis of RNA", Curr Protoc Nucleic Acid Chem. Sep. 2009; Chapter 2: Unit 2.16.1-31.

Berger et al. *Guide to Molecular Cloning Techniques, vol. 152, 1st Ed*. Academic Press, Inc., 1987.

Bhataya et al., "Metabolic engineering of Pichia pastoris X-33 for lycopene production", Process Biochem. Oct. 2009; 44(10): 1095-1102.

Bollinger et al., "Engineering the Diiron Site of *Escherichia coli* Ribonucleotide Reductase Protein R2 to Accumulate an Intermediate Similar to $H_{peroxo}$, the Putative Peroxodiiron(III) Complex from the Methane Monooxygenase Catalytic Cycle", J Am Chem Soc. 1998, 120(5): 1094-1095. Epub Feb. 11, 1998.

Bornscheuer et al., "Survey of Protein Engineering Strategies", Curr Protoc Protein Sci. Nov. 2011; Chapter 26: Unit 26.7.1-14.

Borodina et al., "Mutagenesis of the 'Leucine Gate' to Explore the Basis of Catalytic Versatility in Soluble Methane Monooxygenase", Appl Environ Microbiol. Oct. 2007; 73(20): 6460-6467. Epub Aug. 17, 2007.

Brady, S.F., "Construction of soil environmental DNA cosmid libraries and screening for clones that produce biologically active small molecules", Nat Protoc. 2007; 2(5): 1297-1305.

Brandstetter et al., "Mutational and structural analyses of the regulatory protein B of soluble methane monooxygenase from *Methylococcus capsulatus* (Bath)", Chem Biol. Jul. 1999; 6(7): 441-449.

Braun et al., "14-3-3 (Bmh) Proteins Regulate Combinatorial Transcription following RNA Polymerase II Recruitment by Binding at Adr1-Dependent Promoters in *Saccharomyces Cerevisiae*", Mol Cell Biol. Feb. 2013; 33(4): 712-724. Epub Dec. 3, 2012.

Brouk et al., "Improving Biocatalyst Performance by Integrating Statistical Methods into Protein Engineering", Appl Environ Microbiol. Oct. 2010; 76(19): 6397-6403. Epub Aug. 13, 2010.

Burrows et al., "Substrate Specificities of the Soluble and Particulate Methane Mono-oxygenases of *Methylosinus trichosporium* OB3b", J Gen Microbiol. 1984; 130: 3327-3333.

Callaghan et al., "Residues near the N-terminus of protein B control autocatalytic proteolysis and the activity of soluble methane monooxygenase", Eur J Biochem. Apr. 2002; 269(7): 1835-1843.

Canada et al., "Directed Evolution of Toluene ortho-Monooxygenase for Enhanced 1-Naphthol Synthesis and Chlorinated Ethene Degradation", J Bacteriol. Jan. 2002; 184(2): 344-349.

Carvalho et al., "The remarkable *Rhodococcus erythropolis*", Appl Microbiol Biotechnol. Jun. 2005; 67(6): 715-726. Epub Feb. 15, 2005.

Cereghino et al., "Heterologous protein expression in the methylotrophic yeast Pichia pastoris", FEMS Microbiol Rev. Jan. 2000; 24(1): 45-66.

Chistoserdova et al., "A genomic view of methane oxidation by aerobic bacteria and anaerobic archaea", Genome Biol. 2005; 6(2): 208. Epub Feb. 1, 2005.

Cho et al., "Defective Export of a Periplasmic Enzyme Disrupts Regulation of Fatty Acid Synthesis", J Biol Chem. Mar. 3, 1995; 270(9): 4216-4219.

Chong et al., "Improving Ethanol Tolerance of *Escherichia coli* by Rewiring Its Global Regulator cAMP Recepter Protein (CRP)", PLoS One. 2013; 8(2):e57628. Epub Feb. 28, 2013.

Clark et al., "*Escherichia coli* mutants with altered control of alcohol dehydrogenase and nitrate reductase", J Bacteriol. Jan. 1980; 141(1): 177-183.

Colby et al., "Some Properties of a Soluble Methane Monooxygenase from *Methylococcus capsulatus* Strain Bath", Biochem J. Aug. 1, 1976; 157(2): 495-497.

Colby et al., "The Soluble Methane Mono-oxygenase of *Methylococcus capsulatus* (Bath). Its ability to oxygenate $n$-alkanes, $n$-alkenes, ethers, and alicyclic, aromatic and heterocyclic compounds", Biochem J. Aug. 1, 1977; 165(2): 395-402.

Cole, P.A., "Chaperone-assisted protein expression", Structure. Mar. 15, 1996; 4(3): 239-242.

Coleman et al., "Hydrocarbon monooxygenase in Mycobacterium: recombinant expression of a member of the ammonia monooxygenase superfamily", ISME J. Jan. 2012; 6(1): 171-182. Epub Jul. 28, 2011.

Costas et al., "Dioxygen Activation at Mononuclear Nonheme Iron Active Sites: Enzymes, Models, and Intermediates", Chem Rev. Feb. 2004; 104(2): 939-986.

Coufal et al., "Sequencing and analysis of the *Methylococcus capsulatus* (Bath) soluble methane monooxygenase genes", Eur J Biochem. Apr. 2000; 267(8): 2174-2185.

Cregg et al., "Recombinant Protein Expression in Pichia pastoris", Mol Biotechnol. Sep. 2000; 16(1): 23-52.

Crombie et al., "Trace-gas metabolic versatility of the facultative methanotroph *Methylocella silvestris*", Nature. Jun. 5, 2014; 510(7503): 148-151. Epub Apr. 28, 2014.

Crombie, A., "Metabolism of methane and propane and the role of the glyoxylate bypass enzymes in *Methylocella silvestris* BL2", Doctoral thesis submitted to the School of Life Sciences at the University of Warwick, Coventry, UK, Sep. 2011, 315 pages.

Csáki et al., "Genes involved in the copper-dependent regulation of soluble methane monooxygenase of *Methylococcus capsulatus* (Bath): cloning, sequencing and mutational analysis", Microbiology. Jul. 2003; 149(Pt 7): 1785-1795.

Datsenko et al., "One-step inactivation of chromosomal genes in *Escherichia coli* K-12 using PCR Products", Proc Natl Acad Sci USA. Jun. 6, 2000; 97(12): 6640-6645.

De Vries et al., "Cloning, expression, and sequence analysis of the *Bacillus methanolicus* C1 methanol deydrogenase gene", J Bacteriol. Aug. 1992; 174(16): 5346-5353.

Dedysh et al., "Facultative Methane Oxidizers." in: *Handbook of Hydrocarbon and Lipid Microbiology*, K.N. Timmis (ed.), (Springer-Verlag, Berlin, Heidelberg, 2010), pp. 1968-1976.

Dedysh et al., "*Methylocella* Species Are Facultatively Methanotrophic", J Bacteriol. Jul. 2005; 187(13): 4665-4670.

Duan et al., "High-rate conversion of methane to methanol by *Methylosinus trichosporium* OB3b", Bioresour Technol. Aug. 2011; 102(15): 7349-7353. Epub May 6, 2011.

Duetz et al., "Using proteins in their natural environment: potential and limitations of microbial whole-cell hydroxylations in applied biocatalysis", Curr Opin Biotechnol. Aug. 2001; 12(4): 419-425.

(56) References Cited

OTHER PUBLICATIONS

Elango et al., "Crystal structure of the hydroxylase component of methane monooxygenase from *Methylosinus trichosporium* OB3b", Protein Sci. Mar. 1997; 6(3): 556-568.
Engler et al., "Combinatorial DNA assembly using Golden Gate cloning", Methods Mol Biol. 2013; 1073: 141-156. Abstract only.
Erijman et al., "Transfer-PCR (TPCR): A highway for DNA cloning and protein engineering", J Struct Biol. Aug. 2011; 175(2): 171-177. Epub Apr. 15, 2011.
Eroshin et al., "Influence of Amino Acids, Carboxylic Acids and Sugars on the Growth of *Methylococcus capsulatus* on Methane", J Appl Bacteriol. Dec. 1968; 31(4): 560-567.
Foster et al., "A Methane-Dependent Coccus, with Notes on Classification and Nomenclature of Obligate, Methane-Utilizing Bacteria", J Bacteriol. May 1996; 91(5): 1924-1931.
Fox et al., "Evidence for a μ-Oxo-bridged Binuclear Iron Cluster in the Hydroxylase Component of Methane Monooxygenase. Mössbauer and EPR studies", J Biol Chem. Aug. 5, 1988; 263(22): 10553-10556.
Fox et al., "Methane Monooxygenase from *Methylosinus trichosporium* OB3b", J Biol Chem. Jun. 15, 1989; 264(17): 10023-10033.
Furuya et al., "Reconstitution of Active Mycobacterial Binuclear Iron Monooxygenase Complex in *Escherichia coli*", Appl Environ Microbiol. Oct. 2013; 79(19): 6033-6039. Epub Jul. 26, 2013.
Furuya et al., "The mycobacterial binuclear iron monooxygenases require a specific chaperonin-like protein for functional expression in a heterologous host", FEBS J. Feb. 2013; 280(3): 817-826. Epub Jan. 2, 2013.
Gassner et al., "Component Interactions in the Soluble Methane Monooxygenase System from *Methylococcus capsulatus* (Bath)", Biochemistry. Sep. 28, 1999; 38(39): 12768-12785. Epub Sep. 11, 1999.
Ge et al., "Biological conversion of methane to liquid fuels: Status and opportunities", Biotechnol Adv. Dec. 2014; 32(8): 1460-1475. Epub Oct. 2, 2014.
Gentz et al., "Promoters Recognized by *Escherichia coli* RNA Polymerase Selected by Function: Highly Efficient Promoters from Bacteriophage T5", J Bacteriol. Oct. 1985; 164(1): 70-77.
Gibson et al., "Enzymatic assembly of DNA molecules up to several hundred kilobases", Nat Methods. May 2009; 6(5): 343-345. Epub Apr. 12, 2009.
Glass et al., "Trace metal requirements for microbial enzymes involved in the production and consumption of methane and nitrous oxide", Front Microbiol. Feb. 21, 2012; 3: 61. eCollection 2012.
Gould et al., "Development of the Yeast Pichia pastoris as a Model Organism for a Genetic and Molecular Analysis of Peroxisome Assembly", Yeast. Aug. 1992; 8(8): 613-628.
Graham et al., "Factors Affecting Competition Between Type I and Type II Methanotrophs in Two-organism, Continuous-flow Reactors", Microb Ecol. Jan. 1993; 25(1): 1-17.
Green et al. *Molecular Cloning: A Laboratory Manual, 4th ed.* Cold Spring Harbor, New York, Cold Spring Harbor Laboratory Press, 2012.
Green et al., "Copper ions as inhibitors of protein C of soluble methane monooxygenase *Methylococcus capsulatus* (Bath)", Eur J Biochem. Nov. 15, 1985; 153(1): 137-144.
Green et al., "Substrate Specificity of Soluble Methane Monooxygenase. Mechanistic Implications", J Biol Chem. Oct. 25, 1989; 264(30): 17698-17703.
Green et al., "The Biosynthesis and Assembly of Protein A of Soluble Methane Monooxygenase of *Methylococcus capsulatus* (Bath)", J Biol Chem. Nov. 25, 1988; 263(33): 17561-17565.
Grosse et al., "Purification and Characterization of the Soluble Methane Monooxygenase of the Type II Methanotrophic Bacterium *Methylocystis* sp. Strain WI 14", Appl Environ Microbiol. Sep. 1999; 65(9): 3929-3935.
Haacke et al., "Chaperone over-expression in *Escherichia coli*: Apparent increased yields of soluble recombinant protein kinases are due mainly to soluble aggregates", Protein Expr Purif. Apr. 2009; 64(2): 185-193. Epub Nov. 11, 2008.

Hakemian et al., "The Biochemistry of Methane Oxidation", Annu Rev Biochem. 2007; 76: 223-241.
Han et al., "Partial Oxidative Conversion of Methane to Methanol Through Selective Inhibition of Methanol Dehydrogenase in Methanotrophic Consortium from Landfill Cover Soil", Appl Biochem Biotechnol. Nov. 2013; 171(6): 1487-1499. Epub Aug. 21, 2013.
Hanson et al., "Methanotrophic bacteria", Microbiol Rev. Jun. 1996; 60(2): 439-471.
Hartl et al., "Mitochondrial protein import", Biochim Biophys Acta. Jan. 18, 1989; 988(1): 1-45.
Hartmann et al. *Handbook of RNA Biochemistry: Second, Completely Revised and Enlarged Edition*. Weinheim, Germany, Wiley-VCH, Verlag GmbH & Co. KGaA, 2014.
Hartner et al., "Regulation of methanol utilisation pathway genes in yeasts", Microb Cell Fact. Dec. 14, 2006; 5: 39.
Haynes et al., "Rethinking biological activation of methane and conversion to liquid fuels", Nat Chem Biol. May 2014; 10(5): 331-339. Epub Apr. 17, 2014.
Henne et al., "Construction of Environmental DNA Libraries in *Escherichia coli* and Screening for the Presence of Genes Conferring Utilization of 4-Hydroxybutyrate", Appl Environ Microbiol. Sep. 1999; 65(9): 3901-3907.
Hoefman et al., "Customized media based on miniaturized screening improve growth rate and cell yield of methane-oxidizing bacteria of the genus *Methylomonas*", Antonie Van Leeuwenhoek. Feb. 2014; 105(2): 353-366. Epub Nov. 24, 2013.
Holmes et al., "Evolutionary ecology and multidisciplinary approaches to prospecting for monooxygenases as biocatalysts", Antonie Van Leeuwenhoek. Jun. 2008; 94(1): 75-84. Epub Feb. 19, 2008.
Hoover et al., "Bacterial production of free fatty acids from freshwater macroalgal cellulose", Appl Microbiol Biotechnol. Jul. 2011; 91(2): 435-446. Epub Jun. 4, 2011.
Hoover et al., "Isolation of Improved Free Fatty Acid Overproducing Strains of *Escherichia coli* via Nile Red Based High-Throughput Screening", Environ Prog Sustain Energy. Apr. 2012; 31(1): 17-23. Epub Nov. 17, 2011.
Huang et al., "Determination of the Carbon Kinetic Isotope Effects on Propane Hydroxylation Mediated by the Methane Monooxygenases from *Methylococcus capsulatus* (Bath) by Using Stable Carbon Isotopic Analysis", Chembiochem. Aug. 2, 2002; 3(8): 760-765.
Huang et al., "DFT study of the mechanism for methane hydroxylation by soluble methane monooxygenase (sMMO): effects of oxidation state, spin state, and coordination number", Dalton Trans. Jan. 28, 2013; 42(4): 1011-1023.
Iguchi et al., "Soluble and particulate methane monooxygenase gene clusters of the type I methanotroph *Methylovulum miyakonense* HT12", FEMS Microbiol Lett. Nov. 2010; 312(1): 71-76. Epub Sep. 15, 2010.
Im et al., "Characterization of a novel facultative *Methylocystis* species capable of growth on methane, acetate and ethanol", Environ Microbiol Rep. Apr. 2011; 3(2): 174-181. Epub Aug. 25, 2010.
Innis, M.A. *PCR Protocols: A Guide to Methods and Applications*. San Diego, CA, Academic Press, 1990. Abstract only.
Jahng et al., "Metal ions and chloramphenicol inhibition of soluble methane monooxygenase from *Methylosinus trichosporium* OB3b", Appl Microbiol Biotechnol. Jul. 1996; 45(6): 744-749.
Jiang et al., "Activation of the hydroxylase of sMMO from *Methylococcus capsulatus* (Bath) by hydrogen peroxide", Biochim Biophys Acta. Apr. 21, 1993; 1163(1): 105-112.
Jiang et al., "Chemical modification of the hydroxylase of soluble methane monooxygenase gives one form of the protein with significantly increased thermostability and another that functions well in organic solvents", Biochim Biophys Acta. Sep. 28, 1994; 1201(1): 76-84.
Jiang et al., "Methanotrophs: Multifunctional bacteria with promising applications in environmental bioengineering", Biochem Eng J. May 15, 2010; 49(3): 277-288.
Kalyuzhnaya et al., "Functional metagenomics of methylotrophs", Methods Enzymol. 2011; 495: 81-98.
Kalyuzhnaya et al., "Characterization of a Novel Methanol Dehydrogenase in Representatives of Burkholderiales: Implications

(56) References Cited

OTHER PUBLICATIONS for Environmental Detection of Methylotrophy and Evidence for Convergent Evolution", J Bacteriol. Jun. 2008; 190(11): 3817-3823. Epub Apr. 4, 2008.

Kao et al., "Quantitative Proteomic Analysis of Metabolic Regulation by Copper Ions in *Methylococcus capsulatus* (Bath)", J Biol Chem. Dec. 3, 2004; 279(49): 51554-51560. Epub Sep. 22, 2004.

Kato et al., "The Physiological Role of the Ribulose Monophosphate Pathway in Bacteria and Archaea", Biosci Biotechnol Biochem. Jan. 2006; 70(1): 10-21.

Keel et al., "Large-scale native preparation of in vitro transcribed RNA", Methods Enzymol. 2009; 469: 3-25. Epub Nov. 17, 2009.

Kim et al., "Optimization of Lab Scale Methanol Production by Methylosinus trichosporium OB3b", Biotechnol Bioprocess Eng. Jun. 2010; 15(3): 476-480.

Leahy et al., "Evolution of the soluble diiron monooxygenases", FEMS Microbiol Rev. Oct. 2003; 27(4): 449-479.

Lee et al., "Control of substrate access to the active site in methane monooxygenase", Nature. Feb. 21, 2013; 494(7437): 380-384. Epub Feb. 10, 2013.

Lee et al., "Transient Intermediates of the Methane Monooxygenase Catalytic Cycle", J Biol Chem. Oct. 15, 1993; 268(29): 21569-21577.

Lidstrom et al., "Methylotrophs: Genetics and Commercial Applications", Annu Rev Microbiol. 1990; 44: 27-58.

Lin-Cereghino et al., "Condensed protocol for competent cell preparation and transformation of the methylotrophic yeast *Pichia pastoris*", Biotechniques. Jan. 2005; 38(1): 44-48.

Lin-Cereghino et al., "Mxr1p, a Key Regulator of the Methanol Utilization Pathway and Peroxisomal Genes in Pichia pastoris", Mol Cell Biol. Feb. 2006; 26(3): 883-897.

Lipscomb, J., "Biochemistry of the Soluble Methane Monooxygenase", Annu Rev Microbiol. 1994; 48: 371-399.

Liu et al., "Kinetic and Spectroscopic Characterization of Intermediates and Component Interactions in Reactions of Methane Monooxygenase from *Methylococcus capsulatus* (Bath)", J Am Chem Soc. 1995; 117(41): 10174-10185.

Liu et al., "Spectroscopic Detection of Intermediates in the Reaction of Dioxygen with the Reduced Methane Monooxygenase Hydroxylase from *Methylococcus capsulatus* (Bath)", J Am Chem Soc. 1994; 116(16): 7465-7466.

Lloyd et al., "Heterologous expression of soluble methane monooxygenase genes in methanotrophs containing only particulate methane monooxygenase", Arch Microbiol. May-Jun. 1999; 171(6): 364-370.

Lloyd et al., "Inactivation of the regulatory protein B of soluble methane monooxygenase from *Methylococcus capsulatus* (Bath) by proteolysis can be overcome by a Gly to Gln modification", Eur J Biochem. Aug. 15, 1997; 248(1): 72-79.

Lloyd, J., "Heterologous Expression and Site-Directed Mutagenesis of Soluble Methane Monooxygenase", Doctoral thesis submitted to the Department of Biological Sciences at the University of Warwick, Nov. 1997, 355 pages.

Lontoh et al., "Methane and Trichloroethylene Degradation by *Methylosinus trichosporium* OB3b Expressing Particulate Methane Monooxygenase", Appl Environ Microbiol. Mar. 1998; 64(3): 1106-1114.

Lüers et al., "The Pichia pastoris Dihydroxyacetone Kinase is a PTS1-containing, but Cytosolic, Protein that is Essential for Growth on Methanol", Yeast. Jun. 15, 1998; 14(8): 759-771.

Lund et al., "Electron transfer reactions in the soluble methane monooxygenase of *Methylococcus capsulatus* (Bath)", Eur J Biochem. Mar. 1, 1985; 147(2): 297-305.

Luo et al., "Improved ethanol tolerance in *Escherichia coli* by changing the cellular fatty acids composition through genetic manipulation", Biotechnol Lett. Dec. 2009; 31(12): 1867-1871. Epub Aug. 15, 2009.

Lynch et al., "Mössbauer and EPR Studies of the Binuclear Iron Center in Ribonucleotide Reductase from *Escherichia coli*. A New Iron-to-Protein Stoichiometry", J Biol Chem. May 15, 1989; 264(14): 8091-8096.

Makhoba et al., "Molecular Chaperone Assisted Expression Systems: Obtaining Pure Soluble and Active Recombinant Proteins for Structural and Therapeutic Purposes", J Proteomics Bioinform. Jan. 2015; 8(9): 212-216.

Martinho et al., "Mössbauer Studies of the Membrane-Associated Methane Monooxygenase from *Methylococcus capsulatus* Bath: Evidence for a Diiron Center", J Am Chem Soc. Dec. 26, 2007; 129(51): 15783-15785. Epub Dec. 5, 2007.

McDonald et al., "Diversity of soluble methane monooxygenase-containing methanotrophs isolated from polluted environments", FEMS Microbiol Lett. Feb. 2006; 255(2): 225-232.

Megha et al., "GroEL-GroES assisted folding of multiple recombinant proteins simultaneously over-expressed in *Escherichia coli*", Int J Biochem Cell Biol. Jul. 2015; 64: 277-286. Epub May 6, 2015.

Meinhold et al., "Direct Conversion of Ethane to Ethanol by Engineered Cytochrome", Chembiochem. Oct. 2005; 6(10): 1765-1768.

Membrillo-Hernández et al., "Evolution of the adhE Gene Product of *Escherichia coli* from a Functional Reductase to a Dehydrogenase: Genetic and biochemical studies of the mutant proteins", J Biol Chem. Oct. 27, 2000; 275(43): 33869-33875.

Merkx et al., "Dioxygen Activation and Methane Hydroxylation by Soluble Methane Monooxygenase: A Tale of Two Irons and Three Proteins", Angew Chem Int Ed Engl. Aug. 3, 2001; 40(15): 2782-2807.

Merkx et al., "Why OrfY? Characterization of MMOD, a long overlooked component of the soluble methane monooxygenase from *Methylococcus capsulatus* (Bath)", J Biol Chem. Feb. 22, 2002; 277(8): 5858-5865. Epub Nov. 14, 2001.

Moon et al., "Metabolic engineering of *Escherichia coli* for the production of malic acid", Biochem Eng J. Jun. 2008; 40(2): 312-320.

Müller et al., "NMR Structure of the [2Fe-2S] Ferredoxin Domain from Soluble Methane Monooxygenase Reductase and Interaction with Its Hydroxylase", Biochemistry. Jan. 8, 2002; 41(1): 42-51.

Murrell et al., "Molecular biology and regulation of methane monooxygenase", Arch Microbiol. May-Jun. 2000; 173(5-6): 325-332.

Nazaries et al., "Methane, microbes and models: fundamental understanding of the soil methane cycle for future predictions", Environ Microbiol. Sep. 2013; 15(9): 2395-2417. Epub May 29, 2013.

Nichol et al., "Controlling the Activities of the Diiron Centre in Bacterial Monooxygenases: Lessons from Mutagenesis and Biodiversity", Eur J Inorg Chem. Jul. 2015; 2015(21): 3419-3431.

Nielsen et al., "Regulation of bacterial methane oxidation: transcription of the soluble methane mono-oxygenase operon of *Methylococcus capsulatus* (Bath) is repressed by copper ions", Microbiology. May 1996; 142(Pt 5): 1289-1296.

Nordlund et al., "The active site structure of methane monooxygenase is closely related to the binuclear iron center of ribonucleotide reductase", FEBS Lett. Aug. 3, 1992; 307(3): 257-262.

Oldenhuis et al., "Kinetics of Chlorinated Hydrocarbon Degradation by *Methylosinus trichosporium* OB3b and Toxicity of Trichloroethylene", Appl Environ Microbiol. Jan. 1991; 57(1): 7-14.

Orita et al., "Bifunctional enzyme fusion of 3-hexulose-6-phosphate synthase and 6-phospho-3-hexuloisomerase", Appl Microbiol Biotechnol. Aug. 2007; 76(2): 439-445. Epub May 23, 2007.

Orita et al., "The Archaeon Pyrococcus horikoshii Possesses a Bifunctional Enzyme for Formaldehyde Fixation via the Ribulose Monophosphate Pathway", J Bacteriol. Jun. 2005; 187(11): 3636-3642.

Orita et al., "The Ribulose Monophosphate Pathway Substitutes for the Missing Pentose Phosphate Pathway in the Archaeon Thermococcus kodakaraensis", J Bacteriol. Jul. 2006; 188(13): 4698-4704.

Park et al., "Biological conversion of methane to methanol", Korean J Chem Eng. May 2013; 30(5): 977-987.

(56) References Cited

OTHER PUBLICATIONS

Patel et al., "Purification and Properties of the Hydroxylase Component of Methane Monooxygenase", J Bacteriol. May 1987; 169(5): 2313-2317.

Pilkington et al., "Soluble Methane Monooxygenase from *Methylococcus capsulatus* Bath", Methods Enzymol. 1990; 188: 181-190.

Purich et al. *The Enzyme Reference: A Comprehensive Guidebook to Enzyme Nomenclature, Reactions, and Methods.* Academic Press, 2002. Abstract only.

Ravi et al., "Mechanism of Assembly of the Tyrosyl Radical-Diiron(III) Cofactor of *E. Coli* Ribonucleotide Reductase: 1. Mössbauer Characterization of the Diferric Radical Precursor", J Am Chem Soc. 1994; 116(18): 8007-8014.

Redmond et al., "Identification of novel methane-, ethane-, and propane-oxidizing bacteria at marine hydrocarbon seeps by stable isotope probing", Appl Environ Microbiol. Oct. 2010; 76(19): 6412-6422. Epub Jul. 30, 2010.

Rosenzweig et al., "Geometry of the soluble methane monooxygenase catalytic diiron center in two oxidation states", Chem Biol. Jun. 1995; 2(6): 409-418.

Sazinsky et al., "Product Bound Structures of the Soluble Methane Monooxygenase Hydroxylase from *Methylococcus capsulatus* (Bath): Protein Motion in the α-Subunit", J Am Chem Soc. Apr. 27, 2005; 127(16): 5814-5825. Epub Apr. 2, 2005.

Schrader et al., "Methanol-based industrial biotechnology: current status and future perspectives of methylotrophic bacteria", Trends Biotechnol. Feb. 2009; 27(2): 107-115. Epub Dec. 26, 2008.

Senior et al., "The ICI Single Cell Protein Process", Biotechnol Lett. May 1980; 2(5): 205-210.

Sherman, F., "Getting Started with Yeast", Methods Enzymol. 2002; 350: 3-41.

Sirajuddin et al., "Enzymatic Oxidation of Methane", Biochemistry. Apr. 14, 2015; 54(14): 2283-2294. Epub Apr. 1, 2015.

Smith et al., "Improved System for Protein Engineering of the Hydroxylase Component of Soluble Methane Monooxygenase", Appl Environ Microbiol. Nov. 2002; 68(11): 5265-5273.

Smith et al., "Mutagenesis of Soluble Methane Monooxygenase", Methods Enzymol. 2011; 495: 135-147.

Stafford et al., "rpoN, mmoR and mmoG, genes involved in regulating the expression of soluble methane monooxygenase in Methylosinus trichosporium OB3b", Microbiology. Jul. 2003; 149(Pt 7): 1771-1784.

Takeguchi et al., "Optimization of Methanol Biosynthesis by *Methylosinus trichosporium* OB3b: An Approach to Improve Methanol Accumulation", Appl Biochem Biotechnol. Dec. 1997; 68(3): 143-152.

Tamarit et al., "Identification of the Major Oxidatively Damaged Proteins in *Escherichia coli* Cells Exposed to Oxidative Stress", J Biol Chem. Jan. 30, 1998; 273(5): 3027-3032.

Tin Berg et al., "Dioxygen Activation in Soluble Methane Monooxygenase", Acc Chem Res. Apr. 19, 2011; 44(4): 280-288. Epub Mar. 10, 2011.

Ulrich et al., "Exponential Megapriming PCR (EMP) Cloning—Seamless DNA Insertion into Any Target Plasmid without Sequence Constraints", PLoS One. 2012; 7(12): e53360. Epub Dec. 31, 2012.

Urlacher et al., "Recent advances in oxygenase-catalyzed biotransformations", Curr Opin Chem Biol. Apr. 2006; 10(2): 156-161. Epub Feb. 20, 2006.

Valentine et al., "Mechanistic Studies of the Reaction of Reduced Methane Monooxygenase Hydroxylase with Dioxygen and Substrates", J Am Chem Soc. 1999; 121(16): 3876-3887. Epub Apr. 9, 1999.

Valentine et al., "Principles of small molecule activation by metalloenzymes as exemplified by the soluble methane monooxygenase from *Methylococcus capsulatus* (Bath)", J Chem Soc., Dalton Trans. 1997; 21: 3925-3931.

Van Der Rest et al., "A heat shock following electroporation induces highly efficient transformation of Corynebacterium glutamicum with xenogeneic plasmid DNA", Appl Microbiol Biotechnol. Oct. 1999; 52(4): 541-545.

Vazquez-Duhalt et al. *Petroleum Biotechnology:* Developments and Persepctives. Elsevier Science, 2004.

Vertés et al., "Manipulating Corynebacteria, from Individual Genes to Chromosomes", Appl Environ Microbiol. Dec. 2005; 71(12): 7633-7642.

Wang et al., "Coupling Oxygen Consumption with Hydrocarbon Oxidation in Bacterial Multicomponent Monooxygenases", Acc Chem Res. Sep. 15, 2015; 48(9): 2632-2639. Epub Aug. 21, 2015.

Wang et al., "Electron Transfer Control in Soluble Methane Monooxygenase", J Am Chem Soc. Jul. 9, 2014; 136(27): 9754-9762. Epub Jun. 24, 2014.

Ward et al., "Genomic Insights into Methanotrophy: The Complete Genome Sequence of *Methylococcus capsulatus* (Bath)", PLoS Biol. Oct. 2004; 2(10): e303. Epub Sep. 21, 2004.

Werpy et al., "Top Value Added Chemicals from Biomass. Volume I—Results of Screening for Potential Candidates from Sugars and Synthesis Gas", U.S. Department of Energy, Aug. 2004.

Whittington et al., "Crystal Structures of the Soluble Methane Monooxygenase Hydroxylase from Methylococcus capsulatus (Bath) Demonstrating Geometrical Variability at the Dinuclear Iron Active Site", J Am Chem Soc. Feb. 7, 2001; 123(5): 827-838.

Wood, T. et al, "Active expression of soluble methane monooxygenase from Methylosinus trichosporium OB3b in heterologous hosts", Microbiology. Nov. 2002; 148(Pt 11): 3328-3329.

Woodland et al., "Purification and Characterization of Component A of the Methane Monooxygenase from *Methylococcus capsulatus* (Bath)", J Biol Chem. Jan. 10, 1984; 259(1): 53-59.

Xu et al., "The Heme Monooxygenase Cytochrome $P450_{cam}$ Can Be Engineered to Oxidize Ethane to Ethanol", Angew Chem Int Ed Engl. Jun. 27, 2005; 44(26): 4029-4032.

Yanase et al., "Cloning and sequence analysis of the gene encoding 3-hexulose-6-phosphate synthase from the methylotrophic bacterium, Methylomonas aminofaciens 77a, and its expression in *Escherichia coli*", FEMS Microbiol Lett. Jan. 15, 1996; 135(2-3): 201-205.

Yasueda et al., "*Bacillus subtilis* yckG and yckF Encode Two Key Enzymes of the Ribulose Monophosphate Pathway Used by Methylotrophs, and yckH Is Required for Their Expression", J Bacteriol. Dec. 1999; 181(23): 7154-7160.

Yoon, S., "Towards Practical Application of Methanotrophic Metabolism in Chlorinated Hydrocarbon Degradation, Greenhouse Gas Removal, and Immobilization of Heavy Metals", Doctoral thesis submitted at the University of Michigan, 2010, 158 pages.

Yuan et al., "Modification of the substrate specificity of an acyl-acyl carrier protein thioesterase by protein engineering", Proc Natl Acad Sci USA. Nov. 7, 1995; 92(23): 10639-10643.

Yurimoto et al., "The ribulose monophosphate pathway operon encoding formaldehyde fixation in a thermotolerant methylotroph, *Bacillus brevis* S1", FEMS Microbol Lett. Sep. 10, 2002; 214(2): 189-193.

Zelle et al., "Malic Acid Production by *Saccharomyces cerevisiae*: Engineering of Pyruvate Carboxylation, Oxaloacetate Reduction, and Malate Export", Appl Environ Microbiol. May 2008; 74(9): 2766-2777.

Zhang et al., "L-Malate Production by Metabolically Engineered *Escherichia coli*", Appl Environ Microbiol. Jan. 2011; 77(2): 427-434. Epub Nov. 19, 2010.

Zhang et al., "Metabolic evolution of energy-conserving pathways for succinate production in *Escherichia coli*", Proc Natl Acad Sci USA. Dec. 1, 2009; 106(48): 20180-20185. Epub Nov. 16, 2009.

International Search Report and Written Opinion dated Apr. 3, 2017, in International Patent Application No. PCT/US2016/062623, 13 pages.

Extended European Search Report dated Nov. 9, 2017, in European Patent Application No. 15780357.8, 9 pages.

Communication pursuant to Rule 164(1) EPC, Partial Supplementary European Search Report dated Mar. 14, 2019, in European Patent Application No. 16867180.8, 16 pages.

Extended European Search Report dated Jun. 25, 2019, in European Patent Application No. 16867180.8, 19 pages.

(56) References Cited

OTHER PUBLICATIONS

Rahul Banerfee, Jason C. Jones and John D. Lipscomb, "Soluble Methane Monooxygenase", Annual Reviews, Department of Biochemistry, Molecular Biology, and Biophysics, University of Minnesota, Jan. 11, 2019, 23 pgs.

* cited by examiner

Precursor synthesis

Metabolic routes towards malate (I) Oxaloacetate reduction
$Y_{sp}^{max}$: 2 mol mol$^{-1}$ (II) TCA cycle
$Y_{sp}^{max}$: 1 mol mol$^{-1}$ (III) Glyoxylate route (cyclic)
$Y_{sp}^{max}$: 1 mol mol$^{-1}$ (IV) Glyoxylate route (non-cyclic)
$Y_{sp}^{max}$: 1⅓ mol mol$^{-1}$

SYNTHETIC METHANOTROPHIC AND METHYLOTROPHIC MICROORGANISM AND METHOD THEREOF

CROSS-REFERENCE TO RELATED APPLICATIONS

The present invention is filed under 35 U.S.C. § 371 as the U.S. national phase of International Application No. PCT/US2015/025817, filed Apr. 14, 2015, which designated the U.S. and claims the benefit of U.S. Provisional Application Ser. No. 61/979,512, filed on Apr. 15, 2014, the entire disclosure of which is incorporated herein by reference, including the drawings.

TECHNICAL FIELD

The technology herein pertains to industrial biotechnology and the biological conversion of organic compounds into industrial fuels, chemicals and chemical building blocks.

INTRODUCTION

Petroleum is an unsustainable source of the raw materials used in consumer products and the fuels that power society. Seeking to avoid the scarcity and environmental harms associated with petroleum, researchers have engineered microorganisms that consume sugar and biologically synthesize the fuels and chemicals we need. Although this industry could potentially expand to produce thousands of products that are currently petroleum-sourced, companies are being forced into a narrow focus of developing niche chemicals largely due to a single problem—the high cost of sugar.

Methane is one quarter the price of sugar and it is expected to remain inexpensive for decades. Industrial products made from methane (rather than from sugar or petroleum) by engineered microorganisms may be less expensive to manufacture and have a price advantage in the marketplace.

BRIEF DESCRIPTION OF THE INVENTION

A first aspect of the invention provides a synthetic microorganism, wherein the synthetic microorganism comprises a natural methanol-consuming microorganism and one or more genetic modifications that improve the production of a chemical. In a first embodiment of the first aspect, the natural methanol-consuming microorganism is selected from the group consisting of *Candida boidinii, Hansenula polymorpha, Bacillus methanolicus, Pichia methanolica, Pichia pastoris, Methylobacterium extorquens*. In a second embodiment, the natural methanol-consuming microorganism is selected from the genus *Pichia*. In a third embodiment, the chemical is selected from the group consisting of malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, farnesene, farnesane, squalene, squalane, carotenoids, amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and proteins. In a fourth embodiment, the chemical is a dicarboxylic acid. In a preferred embodiment, the chemical is selected from the group consisting of L-malic acid, D-malic acid, fumaric acid, and succinic acid. In a preferred embodiment, the chemical is L-malic acid. In a fifth embodiment, the genetic modifications comprise one or more gene disruptions. In a preferred embodiment, the gene disruptions are gene deletions. In a sixth embodiment, the genetic modifications comprise the expression of one or more exogenous polynucleotides. In a preferred embodiment, the exogenous polynucleotides are expressed from one or more chromosomal locations. In a preferred embodiment, the exogenous polynucleotides are expressed from one or more plasmid locations. In a preferred embodiment, the exogenous polynucleotides encode a transporter. In a preferred embodiment, the transporter is a malic acid transporter. In a seventh embodiment, the genetic modifications comprise a decreased activity of one or more endogenous enzymes relative to the activity of the wild-type endogenous enzyme. In an eighth embodiment, the genetic modifications comprise an increased activity of one or more endogenous enzymes relative to the activity of the wild-type endogenous enzyme. In a preferred embodiment, the endogenous enzymes are selected from the group of pyruvate carboxylase (EC 6.4.1.1), phosphoenolpyruvate carboxykinase (EC 4.1.1.49), and malate dehydrogenase (EC 1.1.1.37).

In a second aspect, the invention is drawn to a method for producing a chemical, comprising culturing a synthetic microorganism, wherein the synthetic microorganism comprises a natural methanol-consuming microorganism and one or more genetic modifications that improve the production of a chemical, the culturing occurring under suitable culture conditions and for a sufficient period of time to produce the chemical. In a first embodiment of the second aspect the culture medium contains methanol. In a preferred embodiment, the culture medium contains methanol as a major carbon source or as a sole carbon source. In a second embodiment, the chemical is selected from the group consisting of malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, farnesene, farnesane, squalene, squalane, carotenoids, amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and proteins. In a third embodiment, the chemical is a dicarboxylic acid. In a preferred embodiment, the chemical is selected from the group consisting of L-malic acid, D-malic acid, fumaric acid, and succinic acid. In a preferred embodiment, the chemical is L-malic acid. In a fourth embodiment, the chemical is produced at a final concentration of about 1 gram per liter or higher. In a preferred embodiment, the chemical is produced at a final concentration of about 1 gram per liter or higher.

A third aspect of the invention comprises a synthetic microorganism, wherein said synthetic microorganism comprises a natural microorganism and a methanol utilization pathway. In a first embodiment of the third aspect, the natural microorganism is a non-methanol-consuming microorganism. In a preferred embodiment, the natural microorganism is selected from the group consisting of *Escherichia coli, Bacillus subtilis, Pseudomonas putida, Saccharomyces cerevisiae, Corynebacterium glutamicum* and *Salmonella enterica*. In a preferred embodiment, the natural microorganism is not *Corynebacterium glutamicum* or *Escherichia coli*. In a preferred embodiment, the natural microorganism is *Escherichia coli*. In a preferred embodiment, the natural microorganism is *Corynebacterium glutamicum*. In a preferred embodiment, the natural microorganism is *Salmonella enterica*. In a preferred embodiment, the natural microorganism is *Saccharomyces cerevisiae*. In a preferred embodiment, the natural microorganism is *Bacillus subtilis*. In a preferred embodiment, the natural microorganism is *Pseudomonas putida*. In a second embodiment, the methanol utilization pathway comprises one or more exogenous polynucleotides. In a preferred embodiment, the exogenous polynucleotides encode enzymes selected from the group of methanol dehydrogenase (EC 1.1.1.224), 3-hexulose-6-phosphate synthase (EC 4.1.2.43), and 6-phospho-3-hexuloisomerase (EC 5.3.1.27). In a preferred embodiment, the exogenous polynucleotides encode enzymes selected from the group of alcohol oxidase (EC 1.1.3.13), formaldehyde dehydrogenase (EC 1.2.1.46), formate dehydrogenase (EC 1.2.1.2), dihydroxyacetone synthase/formaldehyde transketolase (EC 2.2.1.3), and catalase (EC 1.11.1.6).

In a fourth aspect, the invention is drawn to a method for producing a chemical comprising utilizing a synthetic organism wherein the synthetic organism comprises a natural organism and a methanol utilization pathway under suitable culture conditions and for a sufficient period of time to produce the chemical. In a first embodiment of the fourth aspect, the suitable culture conditions further comprise a culture media containing methanol. In a preferred embodiment, the culture media contains methanol as a major carbon source or as a sole carbon source. In a second embodiment of the fourth aspect, the chemical is selected from the group consisting of malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, farnesene, farnesane, squalene, squalane, carotenoids, amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and proteins. In a third embodiment, the chemical is a dicarboxylic acid. In a preferred embodiment, the chemical is selected from the group consisting of L-malic acid, D-malic acid, fumaric acid, and succinic acid. In a preferred embodiment, the chemical is L-malic acid. In a fourth embodiment, the chemical produced at a final concentration of about 1 gram per liter or higher. In a preferred embodiment, the chemical is produced at a final concentration of about 1 gram per liter or higher.

In a fifth aspect the invention is drawn to a method for producing a biomass, comprising culturing a synthetic microorganism wherein the synthetic organism comprises a natural organism and a methanol utilization pathway under suitable culture conditions and for a sufficient period of time to produce the biomass. In a first embodiment of the fifth aspect, the biomass comprises a single-cell protein or a precursor to single-cell protein.

In a sixth aspect the invention is drawn to a synthetic microorganism, wherein said synthetic microorganism comprises a non-methanotrophic microorganism and one or more genetic modifications that allow said synthetic microorganism to oxidize methane. In a first embodiment of the sixth aspect, the non-methanotrophic organism is a naturally occurring microorganism. In a preferred embodiment, the non-methanotrophic microorganism is selected from the group of *Hansenula, Pichia, Candida*, and *Torulopsis*. In a preferred embodiment, the non-methanotrophic microorganism is selected from the group of *Pichia pastoris* and *Pichia methanolica*. In a preferred embodiment, the non-methanotrophic microorganism is *Escherichia coli*. In a preferred embodiment, the non-methanotrophic microorganism is selected from the group of *Bacillus subtilis, Bacillus methanolicus, Pseudomonas putida, Salmonella enterica* and *Corynebacterium glutamicum*. In a preferred embodiment, the non-methanotrophic microorganism is neither *Corynebacterium glutamicum* nor *Escherichia coli*. In a second embodiment of the sixth aspect, the non-methanotrophic microorganism can grow using methanol as a major carbon source or as sole carbon source. In a third embodiment, the non-methanotrophic organism is a non-naturally occurring microorganism. In a fourth embodiment, the genetic modifications comprise one or more exogenous polynucleotides encoding a methane monooxygenase enzyme. In a preferred embodiment, the exogenous polynucleotides are expressed from one or more chromosomal locations. In a preferred embodiment, the exogenous polynucleotides are expressed from one or more plasmid locations. In a preferred embodiment, the exogenous polynucleotides are expressed from a combination of plasmid locations and chromosome locations. In a preferred embodiment, the methane monooxygenase enzyme is a soluble methane monooxygenase (EC 1.14.13.25). In a preferred embodiment, the soluble methane monooxygenase enzyme is the soluble methane monooxygenase from *Methylococcus capsulatus* (Bath) (ATCC 33009, NCIMB 11132) or *Methylosinus trichosporium* OB3b. (ATCC 35070, NCIMB 11131) In a preferred embodiment, the methane monooxygenase enzyme is a particulate methane monooxygenase (EC 1.4.18.3). In a preferred embodiment, the particulate methane monooxygenase enzyme is the particulate methane monooxygenase from *Methylococcus capsulatus* (Bath) or *Methylosinus trichosporium* OB3b. In a preferred embodiment, the methane monooxygenase enzyme is a non-natural methane monooxygenase. In a preferred embodiment, the non-natural methane monooxygenase enzyme is the spmoB enzyme. In a fifth embodiment of the sixth aspect, the genetic modifications comprise one or more exogenous polynucleotides encoding accessory proteins, helper proteins, or protein-folding chaperones.

In a seventh aspect, the invention comprises a method for producing a chemical, comprising culturing a synthetic microorganism, wherein the synthetic microorganism comprises a non-methanotrophic microorganism and one or more genetic modifications that allow the synthetic microorganism to oxidize methane under suitable culture conditions and for a sufficient period of time to produce said chemical. In a first embodiment of the seventh aspect, the invention further comprises a culture media containing methane. In a second embodiment, the invention further comprises a culture media containing methane and carbon dioxide. In a third embodiment, the chemical is selected from the group consisting of malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, farnesene, farnesane, squalene, squalane, carotenoids, amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and proteins. In a fourth embodiment, the chemical is a dicarboxylic acid. In a preferred embodiment, the chemical is selected from the group consisting of L-malic acid, D-malic acid, fumaric acid, and succinic acid. In a preferred embodiment, the chemical is L-malic acid. In a fifth embodiment, the chemical is produced at a final concentration of about 1 gram per liter or higher. In a preferred embodiment, the chemical is produced at a final concentration of 1 gram per liter or higher In an eighth aspect the invention is drawn to a method for producing biomass, comprising culturing a synthetic microorganism, wherein the synthetic microorganism comprises a non-methanotrophic microorganism and one or more genetic modifications that allow the synthetic microorganism to oxidize methane under suitable culture conditions and for a sufficient period of time to produce said biomass. In a first embodiment, the biomass comprises single-cell protein or a precursor to single-cell protein.

In a ninth aspect, the invention is drawn to a synthetic microorganism, wherein said synthetic microorganism comprises a microorganism and a methane-oxidizing enzyme.

In tenth aspect, the invention is drawn to a synthetic microorganism, wherein said synthetic microorganism comprises a methylotrophic microorganism and a methane-oxidizing enzyme.

DETAILED DESCRIPTION OF THE INVENTION

Figure 1:
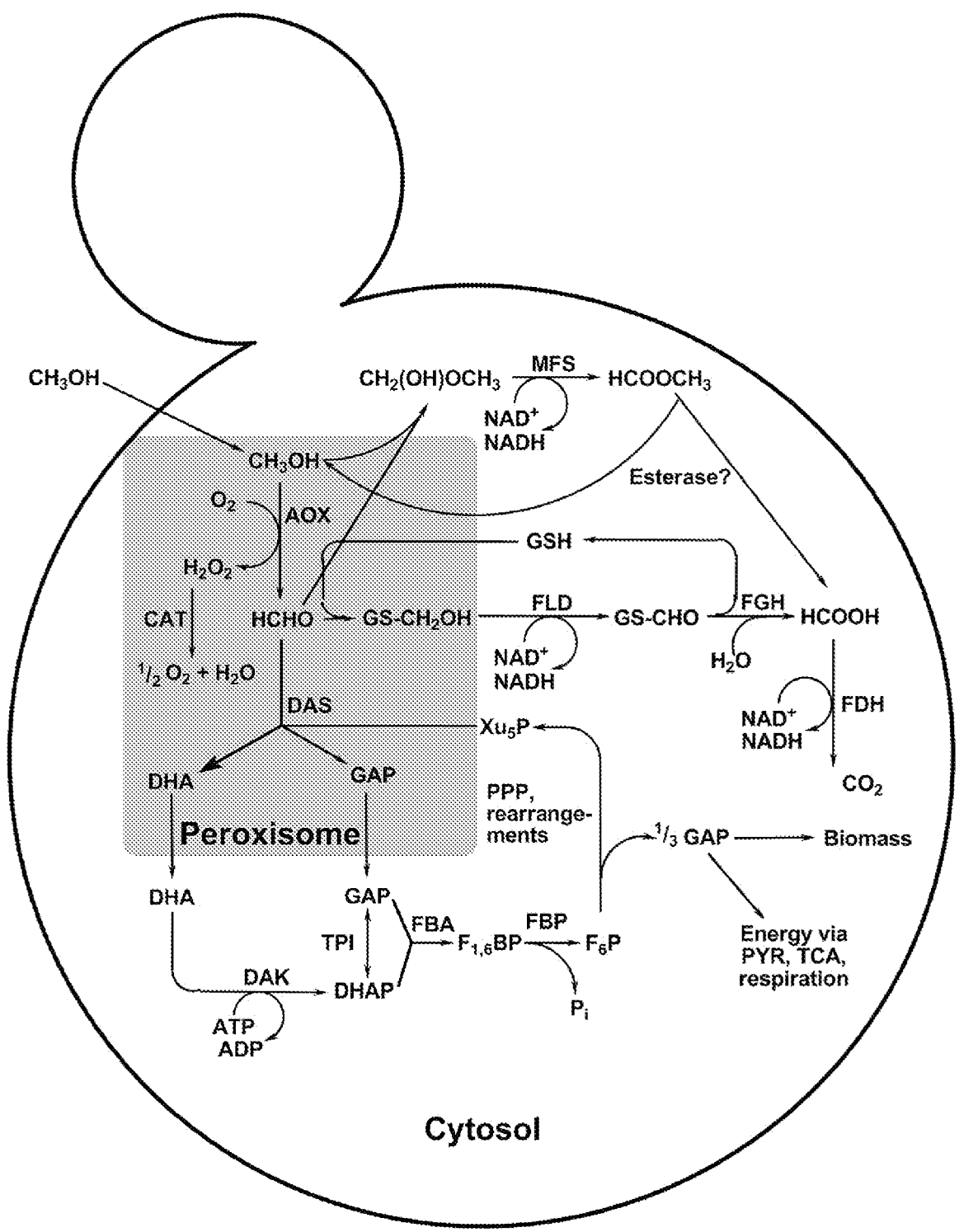
FIG. 1 shows the methanol utilization pathways via xylulose-5-phosphate cycle. The abbreviations in FIG. 1 are defined here: AOX: alcohol oxidase (EC 1.1.3.13), CAT: catalase (EC 1.11.1.6), FLD: formaldehyde dehydrogenase (EC 1.2.1.1), FGH: S-formylglutathione hydrolase (EC 3.1.2.12), FDH: formate dehydrogenase (EC 1.2.1.2), DAS: dihydroxyacetone synthase (EC 2.2.1.3), TPI: triosephosphate isomerase (EC 5.3.1.1), DAK: dihydroxyacetone kinase (EC 2.7.1.29), FBA: fructose 1,6-bisphosphate aldolase (EC 4.1.21.13), FBP: fructose 1,6-bisphosphatase (EC 3.1.3.11), MFS: methylformate synthase; DHA: dihydroxyacetone, GAP: glyceraldehyde 3-phosphate, DHAP: dihydroxyacetone phosphate, F1,6BP: fructose 1,6-bisphosphate, F6P: fructose 6-phosphate, Pi: phosphate, Xu5P: xylulose 5-phosphate, GSH: glutathione, PYR: pyruvate; PPP: pentose phosphate pathway, TCA: tricarboxylic acid cycle. The main pathways and the respective enzymes working in the methanol metabolism in methylotrophic yeasts are shown. Reproduced from (Franz S Hartner & Anton Glieder, *Microbial Cell Factories Regulation of methanol utilisation pathway genes in yeasts*, 21 1-21, 2006).

The disclosure provides microorganisms engineered to consume methane and/or methanol. A synthetic *Escherichia coli* comprising one or more genetic mutations encoding a soluble methane monooxygenase that allows the Escherichia coli to oxidize methane was deposited with the Agricultural Research Culture Collection (NRRL) International Depository Authority located at 1815 N. University Street, Peoria, Illinois, 61604 U.S.A. on Mar. 10, 2020. The accession number for the deposit is NRRL B-67937.

Compositions and methods comprising using said microorganisms to produce chemicals, such as four-carbon dicarboxylic acids, are further provided. The methods provide for superior low-cost production as compared to existing sugar-consuming fermentation.

Unless defined otherwise, all technical and scientific terms used herein have the meaning commonly understood by one of ordinary skill in the art to which this invention belongs. Practitioners are particularly directed to (M R Green and J Sambrook, eds, Molecular Cloning: A Laboratory Manual, 4th ed., Cold Spring Harbor Laboratory Press, 2012), (F M Ausubel, Current Protocols in Molecular Biology (Supplement 99), John Wiley & Sons, New York, 2012), and (Bornscheuer, U. and R. J. Kazlauskas, *Curr Protoc Protein Sci*, 2011). Standard methods also appear in (Bindereif, Schön, & Westhof, Handbook of RNA Biochemistry, Wiley-VCH, Weinheim, Germany, 2005) which describes detailed methods for RNA manipulation and analysis, and (S L Beaucage et al., *Curr Protoc Nucleic Acid Chem*, 2009) and (A Y Keel et al., *Methods Enzymol* 469:3-25, 2009) which describe methods of chemical synthesis and purification of RNA, and are incorporated herein by reference.

Examples of appropriate molecular techniques for generating nucleic acids, and instructions sufficient to direct persons of skill through many cloning exercises are found in (M R Green et al., Guide to Molecular Cloning Techniques, Methods in Enzymology, Volume 152 Academic Press, Inc., San Diego, Calif., 1987); and (PCR Protocols: A Guide to Methods and Applications, Academic Press, San Diego, Calif., 1990), which are incorporated by reference herein.

As used herein, the terms "microbe", "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "naturally occurring" is intended to mean normally found in nature.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions, and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes within a methanol-consuming or methane-consuming pathway.

As used herein, the term "carbon source" is intended to mean a raw material input to an industrial process that contains carbon atoms that can be used by the microorganisms in a culture. For example, industrial cultures of microorganisms may use glucose as a source of carbon atoms. As provided herein, the carbon source can be methane or methanol. In some cases, a culture is grown in a medium containing a single compound that contains carbon atoms. As carbon is an element that is essential for life, the culture must have, in this example, metabolic pathways for converting the single compound containing carbon atoms into all other biological molecules necessary for the organism's survival.

As used herein "sole carbon source" is intended to mean where the suitable conditions comprise a culture media containing either methane or methanol as a carbon source such that, as a fraction of the total carbon atoms in the media, the methane or methanol, respectively, represent about 100% of the total carbon atoms in the media.

As used herein, "major carbon source" is intended to mean that where the suitable conditions comprise a culture media containing methane or methanol as a carbon source as a fraction of the total carbon atoms in the media, the methane or methanol represents, respectively, at least about 10% or more of the total carbon atoms in the media, preferably about 20% or more of the total carbon atoms in the media, preferably about 30% or more of the total carbon atoms in the media, preferably about 40% or more of the total carbon atoms in the media, preferably about 50% or more of the total carbon atoms in the media, preferably about 60% or more of the total carbon atoms in the media, preferably 70% or more of the total carbon atoms in the media, preferably about 80% or more of the total carbon atoms in the media or preferably about 90% or more of the total carbon atoms in the media.

As used herein, the term "natural non-methanol-consuming microorganism" is intended to mean a microorganism that is not able to convert methanol into chemicals or biomass or grow using methanol as a major carbon source or as a sole carbon source and/or energy source. Examples of such microorganisms include, but are not limited to, the following species: *Escherichia coli, Bacillus subtilis, Pseudomonas putida, Saccharomyces cerevisiae, Corynebacterium glutamicum, Salmonella enterica, Klebsiella oxytoca, Anaerobiospirilium succiniciproducens, Actinobacillus succinogenes, Mannheimia succiniciproducens, Rhizobium etli, Gluconobacter oxydans, Zymomonas Lactococcus lactis, Lactobacillus plantarum, Streptomyces coelicolor, Clostridium acetobutylicum, Pseudomonas fluorescens, Schizosaccharomyces pombe, Kluyveromyces lactis, Kluyveromyces marxianus, Aspergillus terreus*, or *Aspergillus niger*.

As used herein, the terms "methylotroph" "methanol-consuming organism", "methylotroph", "methylotrophic microorganism", "methylotrophic organism", and "methylotrophic" are intended to mean any organism that is able to convert methanol (i.e. "methyl alcohol", CH3OH) into a chemical or into biomass or into molecules that the organism can use in its metabolic pathways which generate energy or reducing equivalents so that the organism can grow using methanol as a sole carbon source or major carbon source and/or energy source. For example, some naturally-occurring microorganisms are known to consume methanol by converting it first into formaldehyde, and then subsequently combining the formaldehyde molecule with other molecules in the cell in pathways known as the ribulose monophosphate cycle (RuMP), or the xylulose monophosphate cycle (XuMP), or the serine cycle, or the Calvin-Benson-Bassham cycle (CBB). In another example, some microorganisms are known to consume methanol by converting methanol to formaldehyde, then to formate, then to carbon dioxide, and, in so doing, generate energy. Other pathways that enable organisms to assimilate methanol into metabolism are also possible and this example is not meant to limit the invention to the above-mentioned assimilation pathways.

As used herein, the terms "methanotroph", "methane-consuming organism", "methanotrophic organism", "methanotrophic microorganism", and "methanotrophic" are intended to mean a microorganism that can consume methane as its major carbon source and/or as its sole energy and/or sole carbon source. In contrast, a "non-methanotrophic microorganism" is one that is incapable of survival on methane as a sole carbon source or major carbon source.

As used herein, the term "synthetic methylotroph" is intended to mean a non-methanol consuming microorganism that has been modified to be able to consume methanol as its sole energy and/or sole carbon source and/or major carbon source. Some methylotrophs are naturally occurring, while others, described here in this invention, are synthetic. Synthetic methylotrophs are organisms that are capable of surviving on methanol as a sole carbon source or major carbon source due to the addition of a pathway that allows the assimilation of methanol. Modification may be a genetic modification such as one or more mutations to the microorganisms nucleic acids, the introduction of an episomal plasmid, and/or the introduction of exogenous polynucleotides.

As used herein, the term "synthetic methanotroph" is intended to mean a non-methane consuming microorganism that has been modified to be able to consume methane as its sole energy and/or sole carbon source and/or major carbon source. Some methanotrophs are naturally occurring, while others, described here in this invention, are synthetic. Synthetic methanotrophs are organisms that are capable of surviving on methane as a sole carbon source or major carbon source due to the addition of a pathway that allows the assimilation of methane. Modification may be a genetic modification such as one or more mutations to the microorganisms nucleic acids, the introduction of an episomal plasmid, and/or the introduction of exogenous polynucleotides. Said modification may be a genetic modification such as one or more mutations to the microorganism's nucleic acids, the introduction of an episomal plasmid, and/or the introduction of exogenous polynucleotides.

As used herein, the term "chemical" is broadly meant include any substance used in or resulting from a reaction involving changes to atoms or molecules, especially one derived according to any of the processes set forth herein. As such, a chemical is intended to mean a substance obtained by a chemical process or a substance having a chemical effect, Examples of chemicals contemplated by the invention, without limitation, are dicarboxylic acid, malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, isoprene, farnesene, farnesane, squalene, squalane, carotenoids, amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and proteins. Other examples of chemicals include, but are not limited to, ethanol, propanol, isopropanol, butanol, fatty alcohols, fatty acid esters, ethyl esters, wax esters; hydrocarbons and alkanes such as propane, octane, diesel, Jet Propellant 8 (JP8); polymers such as terephthalate, 1,3-propanediol, 1,4-butanediol, polyols, Polyhydroxyalkanoates (PHA), poly-beta-hydroxybutyrate (PHB), acrylate, adipic acid, ε-caprolactone, isoprene, caprolactam, rubber; commodity chemicals such as lactate, docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, nutraceuticals, polymers, paraffin replacements, personal care products and pharmaceuticals. Other examples of chemical include, without limitation, all compounds that can be produced with the methods set forth herein. Such compounds are intended to include all molecules that can be constructed with the methods set forth herein including, for example without limitation, all organic and inorganic molecules that can be made with the methods set forth herein. The term chemical is intended to include natural and non-natural compounds. Examples of natural molecules include, but are not limited to, amino acids, nucleic acids, nucleotides and polynucleotides and all related biological molecules. Non-natural compounds include, but are not limited to, amino acids and nucleotides that are modified in a way differently than they are normally modified in biological systems.

As used herein, the term "enzyme" is intended to refer to molecules that accelerate or catalyze chemical reactions. Almost all metabolic processes in the cell need enzymes in order to occur at rates fast enough to sustain life, Some of the enzymes useful n the invention are, without limitation, methanol dehydrogenase (EC 1.1.1.224 or 1.1.99.37 or 1.1.2.7), alcohol dehydrogenase (EC 1.1.1.1), 3-hexulose-6-phosphate synthase (EC 4.1.2.43) and 6-phospho-3-hexuloisomerase (EC 5.3.1.27), alcohol oxidase (EC 1.1.3.13), methanol dehydrogenase (EC 1.1.1.224 or 1.1.99.37 or 1.1.2.7), formaldehyde dehydrogenase (EC 1.2.1.46), formate dehydrogenase (EC 1.2.1.2), dihydroxyacetone synthase/formaldehyde transketolase (EC 2.2.1.3), and catalase (EC 1.11.1.6).

As used herein, the terms "dicarboxylic acid" and "diacid" are intended to mean a chemical whose structure includes two carboxylic acid (COOH) chemical groups. Representative examples of dicarboxylic acids include but are not limited to: oxalic acid, malonic acid, succinic acid (butanedioic acid), fumaric acid, maleic acid, malic acid, glutaric acid, adipic acid, pimelic acid, suberic acid, azelaic acid, sebacic acid, undecanedioic acid, dodecanedioic acid.

As used herein, the term "biomass" is intended to mean the collection of biological matter, made up of cells, that results from the culturing process of a microorganism under suitable conditions for the growth of that organism in culture. In some cases, the biomass includes simply the cells and their contents and in some cases, the biomass includes additionally any macromolecules, such as proteins, that are secreted into the culture, outside the boundary of the cell membrane.

As used herein, the term "single-cell protein" is intended to mean a source of mixed protein extracted from pure or mixed cultures of microorganisms. Single-cell protein is used as a substitute for protein-rich foods in human and animal feeds.

As used herein, the term "endogenous polynucleotides" is intended to mean polynucleotides derived from naturally occurring polynucleotides in a given organism. The term "endogenous" refers to a referenced molecule or activity that is present in the host. Similarly, the term when used in reference to expression of an encoding nucleic acid or polynucleotide it refers to expression of the encoding nucleic acid or polynucleotide contained within the microbial organism.

As used herein, the term "exogenous polynucleotides" is intended to mean polynucleotides that are not derived from naturally occurring polynucleotides in a given organism. Exogenous polynucleotides may be derived from polynucleotides present in a different organism. The exogenous polynucleotides can be introduced into the organism by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

As used herein, the term "culturing" is intended to mean the growth or maintenance of microorganisms under laboratory or industrial conditions. The culturing of microorganisms is a standard practice in the field of microbiology. Microorganisms can be cultured using liquid or solid media as a source of nutrients for the microorganisms. In addition, some microorganisms can be cultured in defined media, in which the liquid or solid media are generated by preparation using purified chemical components. The composition of the culture media can be adjusted to suit the microorganism or the industrial purpose for the culture.

As used herein, the term "suitable conditions" is intended to mean any set of culturing parameters that provide the microorganism with an environment that enables the culture to consume the available nutrients. In so doing, the microbiological culture may grow and/or produce chemicals or byproducts. Culturing parameters may include, but are not limited to, such features as the temperature of the culture media, the dissolved oxygen concentration, the dissolved carbon dioxide concentration, the rate of stirring of the liquid media, the pressure in the vessel, etc.

As used herein, the term "sufficient period of time" is intended to mean at least a minimum amount of time required to allow microorganisms in the culture to produce a chemical of interest. Beyond the minimum, a "sufficient period of time" encompasses any amount of time that enables the culture to produce the chemical to a desired level. An industrial-scale culture may require as little as 5 minutes to begin production of detectable amounts of a chemical and some cultures can be productive for several weeks.

As used herein, the term "methanol utilization pathway" is intended to mean at least one enzyme, or a group or set of enzymes, that enable an organism to convert methanol into metabolites that the organism can use as a source of mass (carbon, oxygen and hydrogen atoms) and energy.

As used herein, the terms "accessory protein" and "helper protein" are intended to mean proteins that enable the function of a separate enzyme, collection of enzymes, enzyme complex made of more than one protein, or non-enzymatic protein. One example of the function of an accessory or helper protein is a protein that is known to aid in folding of other proteins (so called "protein folding chaperones" or "chaperonins"). Another example is a protein that modifies another protein, including post-translational modifications such as acetylation, methylation, acylation, farnesylation, etc., as well as the reverse reactions de-acetylation, de-methylation, etc., as well as removing a fraction of a protein. Other examples are proteins that aid an enzyme or enzyme complex in correctly assembling a prosthetic group, or loading a metal center, or enabling the enzyme or complex to become localized to the proper physical location in the cell, or enabling the transfer of electrons or other chemical groups to the enzyme. In some cases, accessory proteins enable the function of an enzyme, even though the exact mechanism of action is not yet known.

As used herein, the term "transporter" is intended to mean a component of the cell that regulates the passage of a chemical, small molecule, or protein across a biological membrane.

As used herein, the term "methane monooxygenase enzyme" is intended to mean the class of enzymes and enzyme complexes capable of oxidizing a carbon-hydrogen bond of the methane molecule to result in a molecule of methanol. Naturally occurring methane-consuming microorganisms have evolved at least two classes of methane monooxygenase enzymes: soluble and particulate. Any enzyme or enzyme complex of these categories, any mutated enzyme or complex, or any researcher-designed enzyme or enzyme complex that converts methane into methanol would be considered a methane monooxygenase enzyme.

Methane is the Ideal Raw Material for Chemical Production

A methane-consuming industrial microorganism may produce fuels and commodity chemicals that are impossible to profitably generate using sugar. Methane is an ideal feedstock for fuel and chemical production due to its low cost, high energy density, abundance in the US, and year-round availability. On a per carbon basis, methane is significantly cheaper and has a 91% higher energy density compared to glucose (enthalpy of combustion).

Enzymes that Transform Methane

The enzymatic pathway to convert methane into biological molecules already exists in nature. "Methanotrophs" can grow using methane as a sole carbon source. Under aerobic conditions, methanotrophs fix methane into central metabolism in three steps: (1) methane is oxidized to methanol; (2) methanol is oxidized to formaldehyde; (3) formaldehyde is assimilated into central metabolism (see, for example, FIG. 2). The enzymes that catalyze these three steps have been extensively characterized over several decades.

Methane monooxygenase (MMO) is the key metalloenzyme that catalyzes the oxidation of methane to methanol by breaking the C—H bond. Methanotrophs can contain two different kinds of MMO: soluble methane monooxygenase (sMMO) and/or membrane-bound particulate methane monooxygenase (pMMO). The two MMOs are not structurally related, and, although both can oxidize methane, they differ in their number of components, substrate ranges, and metal requirements. The regulation and chemistry of both types of MMO enzymes is complex and has been extensively studied.

The pathway from methanol to central metabolites is well-understood in organisms that grow on single-carbon molecules (methylotrophs). Methanol produced by MMO can be oxidized to formaldehyde, catalyzed by the enzyme methanol dehydrogenase (MDH). Several different families of MDH enzymes have been studied, and they differ in their subcellular location, structure, required cofactor(s), and electron acceptor. Formaldehyde is then incorporated into central metabolism by several pathways, including the ribulose monophosphate cycle (RuMP), the xylulose monophosphate cycle (XuMP), the serine cycle, and the Calvin-Benson-Bassham cycle (CBB) The RuMP pathway is the most efficient and produces fructose-6-phosphate, an intermediate in glycolysis. Glycolysis is efficient and fast (N Kato et al., *The physiological role of the ribulose monophosphate pathway in bacteria and archaea*, 70 BIOSCIENCE, BIOTECHNOLOGY, AND BIOCHEMISTRY 10-21, 2006) and enables a methane-utilization pathway with a direct link into the pathway used by sugar-based industrial fermentation strains to produce fuels and chemicals.

Figure 2:
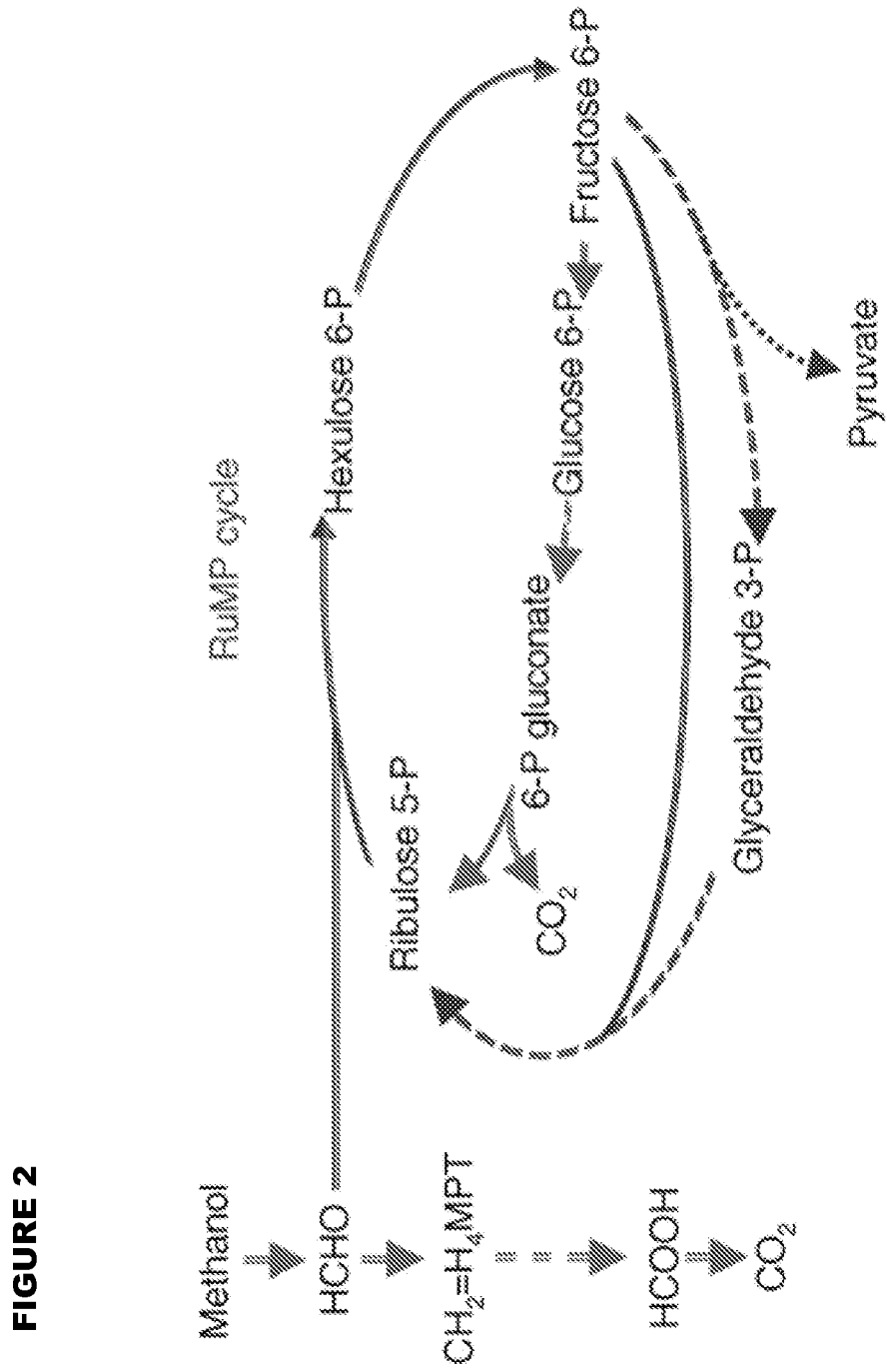
FIG. 2 shows the methanol utilization pathway via the ribulose-5-phosphate cycle. These molecular pathways depict the methanol conversion in a ribulose monophosphate (RuMP)-cycle methylotroph. Examples of dissimilatory pathways which generate energy are shown. Assimilatory pathways generate molecules for building biomass and are also shown. Reproduced from (J Schrader et al., *Methanol-based industrial biotechnology: current status and future perspectives of methylotrophic bacteria*, 27 TRENDS IN BIOTECHNOLOGY 107-115, 2009).

Some microorganisms are able to consume methanol as a sole carbon and energy source, but are unable to consume methane. *Candida boidinii, Hansenula polymorpha, Pichia methanolica, Pichia pastoris, Bacillus methanolicus, Methylobacterium extorquens* AM1 are examples of such microorganisms. In some cases, these strains assimilate methanol through formaldehyde into the xylulose monophosphate (XuMP) pathway (FIG. 1), rather than through the RuMP pathway (FIG. 2).

Engineering Natural Methanotrophs is Difficult

Engineering a natural methanotroph to produce a new chemical is technically challenging at every level of development. There is no precedent for using a natural methanotroph for chemical production at commercial scale. No chemical product pathway has been engineered by expressing heterologous genes in a methanotroph to commercial titer and productivity. Natural methanotrophs are difficult to grow to high cell densities (Z Gou et al., *Functional expression of the particulate methane mono-oxygenase gene in recombinant Rhodococcus erythropolis*, 263 FEMS MICROBIOLOGY LETTERS 136-141, 2006) and metal concentrations must be carefully monitored and adjusted. Many classical strategies to create random mutations work poorly in natural methanotrophs (M E Lidstrom et al., *METHYLOTROPHS: Genetics and commerical applications*, Annual Review Microbiology 27-58, 1990). Known problems include low transformation efficiency of plasmids and endogenous restriction systems that cut foreign DNA. Finally, few genetic techniques exist to engineer these organisms.

Advantages of Developing Synthetic Methanotrophic Microorganisms

Several microorganisms have received the majority of study by microbiologists and metabolic engineers over the past few decades. These model organisms, *Escherichia coli, Saccharomyces cerevisiae, Clostridium acetobutylicum, Corynebacterium glutamicum, Pichia pastoris, Bacillus subtilis, Psuedomonas putida*, and *Chlorella protothecoides*, are the host cells that provide the most flexible, well-understood, genetically tractable starting points for further engineering. A range of tools and techniques has been developed to iteratively construct and evaluate modified derivatives of these strains. The invention of any new core functionality, such as the ability to consume methane, in any of these strains is a significant achievement. A modular genetic component, or set of components, to consume methane may be combined with existing engineered strains to produce a range of industrial products.

Prior Work Expressing MMO in *E. coli* and *S. cerevisiae*

There are no reports of successful methane oxidation in vivo in the model organisms *E. coli* and *S. cerevisiae*. Though some of the MMO components have been expressed in *E. coli*, these components did not assemble into a functional MMO enzyme complex (C A West et al., *Functional expression in Escherichia coli of proteins B and C from soluble methane monooxygenase of Methylococcus capsulatus (Bath)*, 138 JOURNAL OF GENERAL MICROBIOLOGY 1301-1307, 1992).

Advantages of Engineering Methanotrophy in *Pichia*

The industrial yeast *Pichia pastoris* naturally contains most of the genes needed for efficient consumption of methane. As a methylotroph, *Pichia* can grow on methanol as a sole carbon source, using a well-understood, fast pathway. Its genome is sequenced and tools for genetic manipulations are commercially available. In addition, *Pichia* is a sexual yeast which can live in either a haploid or diploid form, with established protocols for mating and sporulation. *Pichia* is related to the model yeast *Saccharomyces cerevisiae*, which has been successfully engineered to produce a wide range of products. *Pichia* is generally regarded as safe (GRAS), and has been successfully used in industrial fermentations for years due to its exceptional ability to express heterologous proteins at high levels (J L Cereghino & J M Cregg, *Heterologous protein expression in the methylotrophic yeast Pichia pastoris.*, 24 FEMS MICROBIOLOGY REVIEWS 45-66, 2000).

*Pichia pastoris* is able to grow on methanol (but not methane) as a sole carbon source via a well-understood, high flux pathway (G P Lin-Cereghino et al., *Mxr1p, a key regulator of the methanol utilization pathway and peroxisomal genes in Pichia pastoris*, 26 MOLECULAR AND CELLULAR BIOLOGY 883-897, 2006), which is transcriptionally up-regulated by the presence of methanol. The enzyme alcohol oxidase (AOX) converts methanol into formaldehyde, which is subsequently either dissimilated into formate and carbon dioxide for energy or assimilated into building block molecules. The assimilation pathway condenses formaldehyde with xylulose-5-phosphate in a cyclic pathway that progresses through the intermediates dihydroxyacetone and glyceraldehyde-3-phosphate. One net molecule of glyceraldehyde-3-phosphate is produced for every three turns of the cycle (FIG. 1) (J L Cereghino et al., *Heterologous protein expression in the methylotrophic yeast Pichia pastoris*, 24 FEMS microbiology reviews 45-66, 2000); (G H. Lüers et al., *The Pichia pastoris dihydroxyacetone kinase is a PTS1-containing, but cytosolic, protein that is essential for growth on methanol*, 14 YEAST 759-771, 1998). The methanol pathway is sufficiently fast that a functional MMO complex in *Pichia* would support a growth rate on methane proportional to the rate of methane oxidation.

Many Industrial Chemical Classes are Possible Commercial Products

Over the last few decades, several companies have successfully commercialized or developed microorganisms capable of producing industrial chemicals from sugar feedstocks. These projects would benefit from reduced feedstock costs, such as being able to use methane instead of sugar. Products currently developed include, but are not limited to, malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, farnesene, farnesane, squalene, squalane, carotenoids, amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and others.

Dicarboxylic Acids

One class of valuable chemical building block molecules is the short-chain dicarboxylic acids (diacids). In 2004, the U.S. Department of Energy identified short-chain diacids, specifically malate, succinate and fumarate, as a top 12 feedstock chemical (T Werpy & G Petersen, *Top Value Added Chemicals from Biomass. Volume I—Results of Screening for Potential Candidates from Sugars and Synthesis Gas*, US Department of Energy, 2004) that can be converted into a diverse array of products such as plastics, resins, fibers, and rubber. Malate, for example, is a safe, natural product found in fruits such as apples and cherries, and is produced in people, animals and plants. Malate, succinate and fumarate are chemically similar molecules which can be easily interconverted using well-known biological and chemical processes. Due to their versatility in commercial applications, any technology to reduce the cost of production would result in wider adoption and expansion of the market opportunity.

In a first aspect, the invention is drawn to a synthetic microorganism, wherein the synthetic microorganism comprises a natural methanol-consuming microorganism and one or more genetic modifications that improve the production of a chemical. In a first embodiment of the first aspect, the natural methanol-consuming microorganism is selected from the group consisting of *Candida boidinii, Hansenula polymorpha, Pichia methanolica, Pichia pastoris, Methylobacterium extorquens*, and *Bacillus methanolicus*. In a second embodiment, the natural methanol-consuming microorganism is selected from the genus *Pichia*. In a third embodiment, the chemical is selected from the group consisting of malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, farnesene, farnesane, squalene, squalane, carotenoids, amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and proteins. In a fourth embodiment, the chemical is a dicarboxylic acid. In a preferred embodiment, the chemical is selected from the group consisting of L-malic acid, D-malic acid, fumaric acid, and succinic acid. In a preferred embodiment, the chemical is L-malic acid. In a fifth embodiment, the genetic modifications comprise one or more gene disruptions. In a preferred embodiment, the gene disruptions are gene deletions. In a sixth embodiment, the genetic modifications comprise the expression of one or more exogenous polynucleotides. In a preferred embodiment, the exogenous polynucleotides are expressed from one or more chromosomal locations. In a preferred embodiment, the exogenous polynucleotides are expressed from one or more plasmid locations. In a preferred embodiment, the exogenous polynucleotides encode a transporter. In a preferred embodiment, the transporter is a malic acid transporter. In a seventh embodiment, the genetic modifications comprise a decreased activity of one or more endogenous enzymes relative to the activity of the wild-type endogenous enzyme. In an eighth embodiment, the genetic modifications comprise an increased activity of one or more endogenous enzymes relative to the activity of the wild-type endogenous enzyme. In a preferred embodiment, the endogenous enzymes are selected from the group of pyruvate carboxylase (EC 6.4.1.1), phosphoenolpyruvate carboxykinase (EC 4.1.1.49), and malate dehydrogenase (EC 1.1.1.37). See, for example, The Enzyme Reference: A Comprehensive Guidebook to Enzyme Nomenclature, Reactions, and Methods" by Daniel L Punch and R. Donald Allison, published in 2002, Academic Press, which is incorporated by reference in its entirety herein, including any drawings.

In a second aspect, the invention is drawn to a method for producing a chemical, comprising culturing a synthetic microorganism, wherein the synthetic microorganism comprises a natural methanol-consuming microorganism and one or more genetic modifications that improve the production of a chemical, the culturing occurring under suitable culture conditions and for a sufficient period of time to produce the chemical. In a first embodiment of the second aspect the culture medium contains methanol. In a preferred embodiment, the culture medium contains methanol as a major carbon source or as a sole carbon source. In a second embodiment, the chemical is selected from the group consisting of malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, farnesene, farnesane, squalene, squalane, carotenoids, amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and proteins. In a third embodiment, the chemical is a dicarboxylic acid. In a preferred embodiment, the chemical is selected from the group consisting of L-malic acid, D-malic acid, fumaric acid, and succinic acid. In a preferred embodiment, the chemical is L-malic acid. In a fourth embodiment, the chemical is produced at a final concentration of about 1 gram per liter or higher. In a preferred embodiment, the chemical is produced at a final concentration of about 1 gram per liter or higher.

A third aspect of the invention comprises a synthetic microorganism, wherein said synthetic microorganism comprises a natural microorganism and a methanol utilization pathway. In a first embodiment of the third aspect, the natural microorganism is a non-methanol-consuming microorganism. In a preferred embodiment, the natural microorganism is selected from the group consisting of *Escherichia coli, Bacillus subtilis, Pseudomonas putida, Saccharomyces cerevisiae, Salmonella enterica, Corynebacterium glutamicum*. In a preferred embodiment, the natural microorganism is *Escherichia coli*. In a preferred embodiment, the natural microorganism is *Saccharomyces cerevisiae*. In a preferred embodiment, the natural microorganism is *Bacillus subtilis*. In a preferred embodiment, the natural microorganism is *Salmonella enterica*. In a preferred embodiment, the natural microorganism is *Corynebacterium glutamicum*. In a preferred embodiment, the natural microorganism is *Pseudomonas putida*. In a preferred embodiment, the natural microorganism is neither *Corynebacterium glutamicum* or *Escherichia coli*. In a second embodiment, the methanol utilization pathway comprises one or more exogenous polynucleotides. In a preferred embodiment, the exogenous polynucleotides encode enzymes selected from the group of methanol dehydrogenase (EC 1.1.1.224), 3-hexulose-6-phosphate synthase (EC 4.1.2.43), and 6-phospho-3-hexuloisomerase (EC 5.3.1.27). In a preferred embodiment, the exogenous polynucleotides encode enzymes selected from the group of alcohol oxidase (EC 1.1.3.13), formaldehyde dehydrogenase (EC 1.2.1.46), formate dehydrogenase (EC 1.2.1.2), dihydroxyacetone synthase/formaldehyde transketolase (EC 2.2.1.3), and catalase (EC 1.11.1.6).

In a fourth aspect, the invention is drawn to a method for producing a chemical utilizing a synthetic organism as provided above under suitable culture conditions and for a sufficient period of time to produce the chemical. In a first embodiment of the fourth aspect, the suitable culture conditions further comprise a culture media containing methanol. In a preferred embodiment, the culture media contains methanol as a sole carbon source. In a second embodiment of the fourth aspect, the chemical is selected from the group consisting of malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, farnesene, farnesane, squalene, squalane, carotenoids, amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and proteins. In a third embodiment, the chemical is a dicarboxylic acid. In a preferred embodiment, the chemical is selected from the group consisting of L-malic acid, D-malic acid, fumaric acid, and succinic acid. In a preferred embodiment, the chemical is L-malic acid. In a fourth embodiment, the chemical is produced at a final concentration of greater than about 10 milligrams per liter, greater than about 100 milligrams per liter, or greater than about 1 gram per liter. In a preferred embodiment, the chemical is produced at a final concentration of greater than 1 about gram per liter, greater than about 5 grams per liter or greater than about 10 grams per liter.

In a fifth aspect the invention is drawn to a method for producing a biomass, comprising culturing a synthetic microorganism as set forth above under suitable culture conditions and for a sufficient period of time to produce the biomass. In a first embodiment of the fifth aspect, the biomass comprises a single-cell protein or a precursor to single-cell protein.

In a sixth aspect the invention is drawn to a synthetic microorganism, wherein said synthetic microorganism comprises a non-methanotrophic microorganism and one or more genetic modifications that allow said synthetic microorganism to oxidize methane. In a first embodiment of the sixth aspect, the non-methanotrophic organism is a naturally occurring microorganism. In a preferred embodiment, the non-methanotrophic microorganism is selected from the group of *Hansenula, Pichia, Candida*, and *Torulopsis*. In a preferred embodiment, the non-methanotrophic microorganism is selected from the group of *Pichia pastoris* and *Pichia methanolica*. In a preferred embodiment, the non-methanotrophic microorganism is *Escherichia coli*. In a preferred embodiment, the non-methanotrophic microorganism is *Salmonella enterica* or *Corynebacterium glutamicum*. In a preferred embodiment, the non-methanotrophic microorganism is selected from the group of *Bacillus subtilis, Bacillus methanolicus, Pseudomonas putida*, and *Corynebacterium glutamicum*. In a preferred embodiment, the non-methanotrophic microorganism is neither *Corynebacterium glutamicum* nor *Escherichia coli*. In a second embodiment of the sixth aspect, the non-methanotrophic microorganism can grow using methanol as a major carbon source or a sole carbon source. In a third embodiment, the non-methanotrophic organism is a non-naturally occurring microorganism. In a fourth embodiment, the genetic modifications comprise one or more exogenous polynucleotides encoding a methane monooxygenase enzyme. In a preferred embodiment, the exogenous polynucleotides are expressed from one or more chromosomal locations. In a preferred embodiment, the exogenous polynucleotides are expressed from one or more plasmid locations. In a preferred embodiment, the exogenous polynucleotides are expressed from a combination of plasmid locations and chromosome locations. In a preferred embodiment, the methane monooxygenase enzyme is a soluble methane monooxygenase (EC 1.14.13.25). In a preferred embodiment, the soluble methane monooxygenase enzyme is the soluble methane monooxygenase from *Methylococcus capsulatus* (Bath) or *Methylosinus trichosporium* OB3b. In a preferred embodiment, the methane monooxygenase enzyme is a particulate methane monooxygenase (EC 1.4.18.3). In a preferred embodiment, the particulate methane monooxygenase enzyme is the particulate methane monooxygenase from *Methylococcus capsulatus* (Bath) or *Methylosinus trichosporium* OB3b. In a preferred embodiment, the methane monooxygenase enzyme is a non-natural methane monooxygenase. In a preferred embodiment, the non-natural methane monooxygenase enzyme is the spmoB enzyme. In a fifth embodiment of the sixth aspect, the genetic modifications comprise one or more exogenous polynucleotides encoding accessory proteins, helper proteins, or protein-folding chaperones.

There are three currently known classes of MMO enzymes: soluble MMO (sMMO), particulate MMO (pMMO), and spmoB (L Nazaries et al., *Methane, microbes and models: Fundamental understanding of the soil methane cycle for future predictions*, 15 ENVIRONMENTAL MICROBIOLOGY 2395-2417, 2013); (R Balasubramanian et al., *Oxidation of methane by a biological dicopper centre*, 465 NATURE 115-119, 2010). The sMMO enzyme complex from *M. capsulatus* (Bath) has been most well-studied in vitro, and consists of 5 or 6 polypeptide chains. The active site is a diiron site that activates dioxygen into a reactive species that can then displace a hydrogen on the methane substrate. The particulate MMO enzyme complex consists of 3 unique polypeptides which come together at the cell membrane. The active site appears to contain a copper atom, critical to the enzyme's function. A fraction of one of these polypeptides was truncated and rearranged to produce a soluble unit, named spmoB, and shown to be functional in vitro [CSL STYLE ERROR: reference with no printed form]. In principle, other MMOs are possible. Given advances in computational protein design, an enzyme that performs similar chemistry could possibly be adapted to oxidize methane instead of its natural substrate. Alternatively, some researchers have had success computationally designing proteins de novo, and one can imagine a novel MMO being discovered in this way. In most cases, the MMO requires metal ions, oxygen molecules, a source of reducing equivalents or energy, and sometimes other chemical groups (e.g. FAD) or protein factors that aid in assembling the complex or in transferring electrons to the active site.

The scope of this invention is meant to include functional equivalents when enzymes are recited as part of the claims. Functionally equivalent molecules may include nucleic acids and/or nucleotides or biologically equivalent proteins and/or polypeptides. Such molecules may, for example without imitation, encode molecules that have an activity that is equivalent to the activity of an MMO enzyme. Such functionally equivalent molecules may be peptides, for example, that are analogues and/or variants by virtue of having amino acid sequences differing from the MMO from which they are derived by virtue of the addition, deletion or substitution of one or more amino acids to result in an amino acid sequence that is preferably at least 60%, more preferably at least 80%, particularly preferably at least 85, 90, 95, 98, 99 or 99.9% identical to the amino acid sequence of the original MMO.

In a seventh aspect, the invention comprises a method for producing a chemical, comprising culturing any of the synthetic microorganisms provided herein under suitable culture conditions and for a sufficient period of time to produce said chemical. In a first embodiment of the seventh aspect, the invention further comprises a culture media containing methane. In a second embodiment, the invention further comprises a culture media containing methane and carbon dioxide. In a third embodiment, the chemical is selected from the group consisting of malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, farnesene, farnesane, squalene, squalane, carotenoids, amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and proteins. In a fourth embodiment, the chemical is a dicarboxylic acid. In a preferred embodiment, the chemical is selected from the group consisting of L-malic acid, D-malic acid, fumaric acid, and succinic acid. In a preferred embodiment, the chemical is L-malic acid. In a fifth embodiment, the chemical is produced at a final concentration of about 1 gram per liter or higher. In a preferred embodiment, the chemical is produced at a final concentration of 1 gram per liter or higher.

In an eighth aspect the invention is drawn to a method for producing biomass, comprising culturing a synthetic microorganism as provided above under suitable culture conditions and for a sufficient period of time to produce said biomass. In a first embodiment, the biomass comprises single-cell protein or a precursor to single-cell protein.

In a ninth aspect, the invention is drawn to a synthetic microorganism, wherein said synthetic microorganism comprises a microorganism and a methane oxidizing enzyme.

In tenth aspect, the invention is drawn to a synthetic microorganism, wherein said synthetic microorganism comprises a methylotrophic microorganism and a methane oxidizing enzyme.

EXAMPLES

The following examples are intended to illustrate but not limit the presently claimed invention.

Example 1. Natural Methylotrophs Producing Valuable Industrial Chemicals: Malate This example describes exemplary pathways to increase production of malate (also known as malic acid) in *Pichia pastoris*.

The yeast model organism *Pichia pastoris* accumulates pyruvate under a variety of conditions such as aerobic conditions and carbon source excess. Previous work has shown in *S. cerevisiae* that cytosolic overexpression of two proteins pyruvate carboxylase (EC 6.4.1.1, Pyc2p, in *S. cerevisiae* S288C=YBR218C, NC_001134.8) and malate dehydrogenase truncated by three C-terminal residues (EC 1.1.1.37, Mdh3(delta-SKL)p, in *S. cerevisiae* S288C=YDL078C, NC_001136.10) along with the overexpression of the malate transporter from *S. pombe* (Mae 1p, NM_001020205, GI:429243562) leads to significant titers, yields, and productivity of malic acid see for example Zelle & Hulster, which is which is incorporated by reference herein in its entirety, including any drawings. These three proteins increase the flux from pyruvate to malic acid. Alternative to the *S. cerevisiae* genes PYC2 and MDH3, overexpression of the equivalent genes from *Pichia pastoris* can also generate the same pathway: PYC2 (PAS_chr2-2_0024), MDH3(delta-SKL) (PAS_chr4_0815). Other PYC2, MDH3, and MAE1 homologs may be tested for improved pathway flux. (see, for example, Table 1)

TABLE 1

| Gene Name | Organism | Gene Acession Number |
|---|---|---|
| PYC2 | *P. pastoris* | PAS_chr2-2_0024 |
| MDH3 | *P. pastoris* | PAS_chr4_0815 |
| SpMAE1 | *S. pombe* | GI:429243562 |
| PYC2 | *S. cerevisiae* S288C | YBR218C, NC_001134.8 |
| MDH3 | *S. cerevisiae* S288C | YDL078C, NC_001136.10 |

A similar pathway in the methylotrophic, Crabtree-negative yeast *Pichia pastoris* could be constructed with the same enzymes. Methods for genetically modifying *Pichia pastoris*, including deletions, insertions, episomal plasmid transformations, etc., are well-established (J Araya-Garay et al., *Construction of a novel Pichia pastoris strain for production of xanthophylls*, 2 AMB EXPRESS 24, 2012); (A Bhataya et al., *Metabolic engineering of Pichia pastoris X-33 for lycopene production*, 44 PROCESS BIOCHEMISTRY 1095-1102, 2009) and commercial strains and protocols are publicly available. Using these methods, a pyruvate carboxylase may be expressed in *Pichia pastoris* from a yeast promoter from either a chromosomal locus or from an episomal plasmid or from both a chromosomal locus and a plasmid. Additionally, a malate dehydrogenase may be expressed in *Pichia pastoris* from a yeast promoter from either a chromosomal locus or from an episomal plasmid or from both a chromosomal locus and a plasmid. Additionally, a malate transporter may be expressed in *Pichia pastoris* from a yeast promoter from either a chromosomal locus or from an episomal plasmid or from both a chromosomal locus and a plasmid. All of these genetic elements can be expressed in the same cell individually or in any combination to improve malate titer, yield, and productivity. Furthermore, the individual enzymatic steps can be increased using methods to improve the activity of the enzymes, such as directed evolution, or by further increasing expression, or by integrating multiple copies of the gene's DNA or by utilizing stronger promoters or by utilizing more efficient transcriptional termination or by stabilizing the mRNA transcript or by increasing the translational efficiency of the open reading frame or by stabilizing the protein polypeptide or by stabilizing the protein folding. Even further improvements may be seen by balancing the expression of the enzymes in the pathway, relative to one another. Pathway balancing can be achieved using libraries of yeast promoters in front of each gene and constructing strain libraries with a range of gene expression for each enzyme. These libraries can subsequently be screened for improvements in titer, yield and productivity.

The methods for molecular biology and culturing *P. pastoris*, see for example (J Araya-Garay et al. *Construction of a novel Pichia pastoris strain for production of xanthophylls*, AMB Express 2:24, 2012) and (Bhataya et al. *Metabolic engineering of Pichia pastoris X-33 for lycopene production*. Process Biochemistry 44: 1095-1102, 2009) each of which is incorporated by reference herein in their entirety, including any drawings, and for malate analysis, see for example (X Zhang et al., *Metabolic evolution of energy-conserving pathways for succinate production in Escherichia coli*, 106 PROCEEDINGS OF THE NATIONAL ACADEMY OF SCIENCES OF THE UNITED STATES OF AMERICA 20180-20185, 2009); (X Zhang et al., *L-Malate production by metabolically engineered Escherichia coli*, 77 APPLIED AND ENVIRONMENTAL MICROBIOLOGY 427-434, 2011); (S Y Moon et al., *Metabolic engineering of Escherichia coli for the production of malic acid*, 40 BIOCHEMICAL ENGINEERING JOURNAL 312-320, 2008) each of which is incorporated by reference herein in their entirety, are described elsewhere in the scientific literature and are evident to one skilled in the art. Briefly, *P. pastoris* can be cultured in rich media or minimal salts media with methanol as the sole carbon and energy source. Culturing for 24 to 72 hrs or longer in shake flasks at 30 degrees Celsius provides the cells with time to produce malate at measurable titers. The cells are removed by centrifugation and the supernatant broth is analyzed by high-performance liquid chromatography (HPLC).

Figure 3:
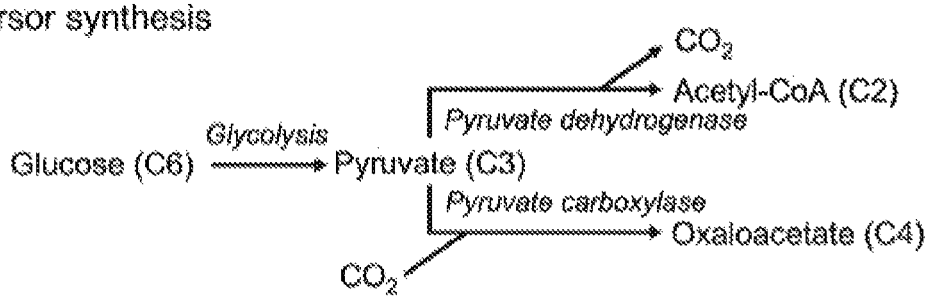
FIG. 3 shows four possible pathways for malate production, using oxaloacetate and/or acetyl-CoA as precursors. (I) Direct reduction of oxaloacetate. (II) Oxidation of citrate via the TCA cycle. (III) Formation from acetyl-CoA via the cyclic glyoxylate route. (IV) Formation from acetyl-CoA and oxaloacetate via the noncyclic glyoxylate route. The abbreviations in FIG. 3 are defined here: OAA, oxaloacetate; MAL, malate; CIT, citrate; ICI, isocitrate; AKG, alpha-ketoglutarate; SUCC, succinyl-CoA; SUC, succinate; FUM, fumarate; C2, acetyl-CoA; Yspmax, maximum theoretical yield (in mol malate per mol glucose). Reproduced from (RM Zelle & Erik De Hulster, *Malic acid production by Saccharomyces cerevisiae: engineering of pyruvate carboxylation, oxaloacetate reduction, and malate export*, APPLIED AND ENVIRONMENTAL MICROBIOLOGY, 2008).
Figure 3:
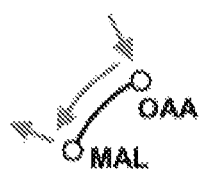
Figure 3:
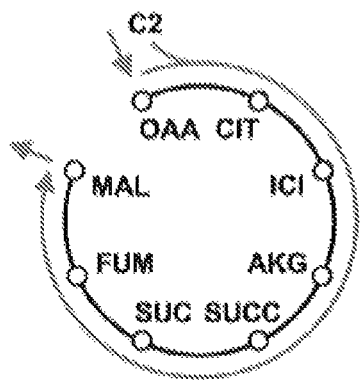
Figure 3:
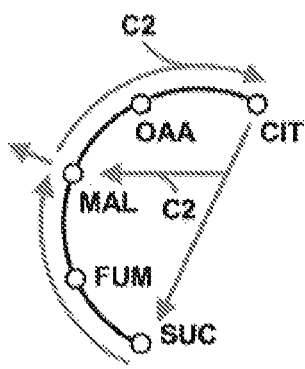
Figure 3:
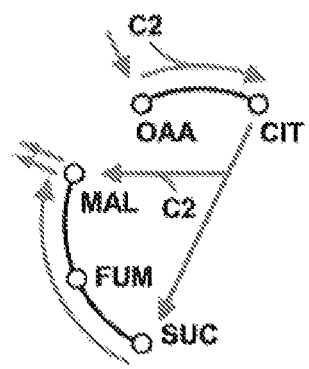

There are four pathways to malate from pyruvate, as described in for example (R M Zelle et al., *Malic acid production by Saccharomyces cerevisiae: Engineering of pyruvate carboxylation, oxaloacetate reduction, and malate export*, 74 APPLIED AND ENVIRONMENTAL MICROBIOLOGY 2766-2777, 2008) which is incorporated by reference herein, including any drawings, and reproduced in FIG. 3. In some cases, the pathway described above from oxaloacetate reduction to malate may be preferable because it has the highest mass yield. However, any of the other 3 pathways would also be able to produce malate from pyruvate, just at a lower mass yield.

Malic acid is converted to other molecules in the yeast cell by enzymes such as fumarase (PAS_chr3_0647 EC 4.2.1.2). Fumarase can be genetically deleted or attenuated or modified and tested for improvements. In addition, side pathways that consume pyruvate or oxaloacetate can be deleted or attenuated or modified and tested for improvements.

Example 2. Synthetic Methylotroph Derived from *E. coli*

This example describes the construction of a genetically engineered host cell wherein the expression of exogenous genes coding for MDH (methanol dehydrogenase), HPS (hexulose-phosphate synthase) and PHI (phospho-hexuloisomerase) in *E. coli* results in a cell capable of growth on methanol.

MDH, HPS and PHI homologues have been previously expressed in *E. coli* and shown to be functional (H Yanase et al., *Cloning and sequence analysis of the gene encoding 3-hexulose-6-phosphate synthase from the methylotrophic bacterium, Methylomonas aminofaciens 77a, and its expression in Escherichia coli*, 135 FEMS MICROBIOLOGY LETTERS 201-205, 1996); (H Yasueda et al., *Bacillus subtilis yckG and yckF encode two key enzymes of the ribulose monophosphate pathway used by methylotrophs, and yckH is required for their expression*, 181 JOURNAL OF BACTERIOLOGY 7154-7160, 1999); (H Yurimoto et al., *The ribulose monophosphate pathway operon encoding formaldehyde fixation in a thermotolerant methylotroph, Bacillus brevis S1*, 214 FEMS MICROBIOLOGY LETTERS 189-193, 2002); (I Orita et al., *The ribulose monophosphate pathway substitutes for the missing pentose phosphate pathway in the archaeon Thermococcus kodakaraensis*, 188 JOURNAL OF BACTERIOLOGY 4698-4704, 2006); (I Orita et al., *Bifunctional enzyme fusion of 3-hexulose-6-phosphate synthase and 6-phospho-3-hexuloisomerase*, 76 APPLIED MICROBIOLOGY AND BIOTECHNOLOGY 439-445, 2007); (G E De Vries et al., *Cloning, expression, and sequence analysis of the Bacillus methanolicus C1 methanol dehydrogenase gene*, 174 JOURNAL OF BACTERIOLOGY 5346-5353, 1992); (E Antoine et al., *Cloning and over-expression in Escherichia coli of the gene encoding NADPH group III alcohol dehydrogenase from Thermococcus hydrothermalis. Characterization and comparison of the native and the recombinant enzymes*, 264 EUROPEAN JOURNAL OF BIOCHEMISTRY 880-889, 1999); (M G Kalyuzhnaya et al., *Characterization of a novel methanol dehydrogenase in representatives of Burkholderiales: Implications for environmental detection of methylotrophy and evidence for convergent evolution*, 190 JOURNAL OF BACTERIOLOGY 3817-3823, 2008). These homologues are amplified directly from the donor host by PCR, or obtained by gene synthesis. Gene synthesis allows the flexibility of codon-optimizing the gene for optimal expression in *E. coli*. These genes are tested as a single operon on a plasmid, or as three different operons on a plasmid. Different expression levels are tested by changing the copy number of the plasmid, or by using different promoters. Alternatively, the three genes are expressed from a single integrated operon, or as three separate integrated operons.

MDH homologues are drawn from the microorganisms *Bacillus methanolicus*, *Thermococcus hydrothermalis*, *Methyloversatilis universalis*, *Methylophilus methylotrophus*, and *Psuedomonas aeruginosa* (G E De Vries et al., *Cloning, expression, and sequence analysis of the Bacillus methanolicus C1 methanol dehydrogenase gene*, 174 Journal of Bacteriology 5346-5353, 1992); (E Antoine et al., *Cloning and over-expression in Escherichia coli of the gene encoding NADPH group III alcohol dehydrogenase from Thermococcus hydrothermalis. Characterization and comparison of the native and the recombinant enzymes*, 264 European Journal of Biochemistry 880-889, 1999); (M G Kalyuzhnaya et al., *Characterization of a novel methanol dehydrogenase in representatives of Burkholderiales: Implications for environmental detection of methylotrophy and evidence for convergent evolution*, 190 Journal of Bacteriology 3817-3823, 2008). HPS and PHI homologues are found as individual proteins or protein fusions in the microorganisms *Methylomonas aminofaciens*, *Bacillus subtilis*, *Bacillus brevis*, *Pyrococcus horikoshii*, *Thermococcus kodakaraensis*, and *Mycobacterium gastri* (H Yanase et al., Cloning and sequence analysis of the gene encoding 3-hexulose-6-phosphate synthase from the methylotrophic bacterium, Methylomonas aminofaciens 77a, and its expression in Escherichia coli, 135 FEMS Microbiology Letters 201-205, 1996); (H Yasueda et al., Bacillus subtilis yckG and yckF encode two key enzymes of the ribulose monophosphate pathway used by methylotrophs, and yckH is required for their expression, 181 Journal of Bacteriology 7154-7160, 1999); (H Yurimoto et al., The ribulose monophosphate pathway operon encoding formaldehyde fixation in a thermotolerant methylotroph, Bacillus brevis S1, 214 FEMS Microbiology Letters 189-193, 2002); (I Orita et al., The archaeon Pyrococcus horikoshii possesses a bifunctional enzyme for formaldehyde fixation via the ribulose monophosphate pathway, 187 JOURNAL OF BACTERIOLOGY 3636-3642, 2005).

Different combinations of the MDH, HPS and PHI may be made as set forth above. Additional genes may be tested, after being identified by a computational method such as BLAST or metagenomics. Their expression may be either from constitutive promoters, such as the T5 promoter, or from an inducible promoter, such as the trc promoter (R Gentz et al., Promoters Recognized by Escherichia coli RNA Polymerase Selected by Function: Highly Efficient Promoters from Bacteriophage T5, 164 Journal of Bacteriology 70-77, 1985); (E Amann et al., Tightly regulated tac promoter vectors useful for the expression of unfused and fused proteins in Escherichia coli, 69 GENE 301-315, 1988).

The combination of three genes that leads to the fastest growth on methanol may be identified by comparing the growth rates between strains containing the different combinations. This may be done by measuring colony size after growth on methanol supplemented minimal agar plates, or in 96-well liquid plates using $OD_{600}$ measurements where the media is minimal media supplemented with methanol. The minimal media may be M9 minimal media containing appropriate antibiotics and necessary supplements.

Example 3. Synthetic Methylotroph Derived from S. cerevisiae

This example provides exemplary pathways for a methanol-consuming pathway in Saccharomyces cerevisiae.

This example describes two specific embodiments of S. cerevisiae strains capable of methanol-consumption. In the first embodiment, S. cerevisiae may be endowed with the methanol-consumption pathway of P. pastoris via standard molecular cloning and metabolic engineering. The methanol-consumption pathway of P. pastoris consists of the enzymes alcohol oxidase (EC 1.1.3.13, Aox1, Aox2), formaldehyde dehydrogenase (EC 1.2.1.46, Fld), formate dehydrogenase (EC 1.2.1.2, Fdh), dihydroxyacetone synthase (EC 2.2.1.3, Dhas), and catalase (EC 1.11.1.6, Cat). These genes may be expressed from chromosomal integrated loci or from plasmids or both using S. cerevisiae promoters, such as Pcyc1, Padh1, Ptef2, Pgal1. Other homologues of these genes may be identified using algorithms such as BLAST and are tested in the same manner. These genes may be expressed in different combinations in S. cerevisiae. The resultant strains containing combinations of these genes may be tested for growth in minimal media supplemented with methanol. Strains that grow on methanol have functional methanol-consumption pathways.

Due to the localization of certain enzymes to the peroxisomal subcellular compartment, pathway enzymes, such as but not limited to Aox1, Aox2, Dhas, and Cat, are targeted to the peroxisome. Additionally, peroxisomal assembly proteins present in P. pastoris (but absent in S. cerevisiae) may be required or helpful for the methanol-consumption pathway (S J Gould et al., Development of the yeast Pichia pastoris as a model organism for a genetic and molecular analysis of peroxisome assembly, 8 YEAST (CHICHESTER, ENGLAND) 613-628, 1992). In addition, the S. cerevisiae transcription factor Adr1p is the homolog of the P. pastoris Mxr1p transcription factor known to be activated by growth in methanol. As such, promoters activated by Mxr1p in P. pastoris, such as Paox1, and promoters activated by Adr1p in S. cerevisiae, such as Padh2, Pgut1, Ppox1 and many others may be tested (K a Braun et al., 14-3-3 (Bmh) proteins regulate combinatorial transcription following RNA polymerase II recruitment by binding at Adr1-dependent promoters in Saccharomyces cerevisiae, 33 MOLECULAR AND CELLULAR BIOLOGY 712-24, 2013). Genes encoding the enzymes Aox1p, Aox2p, Dhas, and Cat, as well as peroxisomal proteins and any other helper proteins, may be cloned from P. pastoris using standard molecular biology techniques (F Sherman, Getting Started with Yeast, 350 METHODS IN ENZYMOLOGY 3-41, 2002).

In another embodiment, a methanol-consuming pathway may be constructed using the genes described above in Example 2 using the RuMP pathway. These genes, MDH, HPS, and PHI and homologs of these derived from organisms listed above or those found in computational searches of genomic data, may be expressed in S. cerevisiae. As in the embodiment described above, S. cerevisiae promoters and plasmids may be used to express the genes in various combinations. Modifications of the RuMP pathway may be made with genetic changes using standard techniques to, for example, alter the promoter strength.

Example 4. Synthetic Methanotroph Derived from P. pastoris

This example provides a description of a strain of P. pastoris capable of growth on methane as a sole carbon and energy source.

Since P. pastoris is naturally capable of growth on methanol, an engineered strain of P. pastoris expressing a functional MMO enzyme or enzyme complex consumes methane as a sole carbon and energy source for the purposes of generating biomass or of producing fuels or chemicals may be created. There are three known categories of MMOs: soluble MMOs, particulate MMOs, and hybrid MMOs (L Nazaries et al., Methane, microbes and models: Fundamental understanding of the soil methane cycle for future predictions, 15 ENVIRONMENTAL MICROBIOLOGY 2395-2417, 2013); (R Balasubramanian et al., Oxidation of methane by a biological dicopper centre, 465 NATURE 115-119, 2010). The sMMOs and pMMOs may be cloned from genomic DNA of organisms such as Methylococcus capsulatus (Bath) or Methylosinus trichosporium OB3b, or chemically synthesized, as described herein. The hybrid MMO spmoB was designed from the soluble fragment of the pmoB subunit of the pMMO and shown to be functional in vitro (R Balasubramanian et al., Oxidation of methane by a biological dicopper centre, 465 NATURE 115-119, 2010). All MMOs, such as sMMOs, pMMOs and spmoB, may be cloned into P. pastoris using standard molecular biology techniques. Promoters may be selected from the lists in Example 3 and strains may be built by transformation of P. pastoris or derivatives using standard methods. See, for example, Table 2.

TABLE 2

| Gene Name | Organism | Accession Number |
|---|---|---|
| mmoX | *Methylococcus capsulatus* (Bath) | GI:7770066 |
| mmoY | *Methylococcus capsulatus* (Bath) | GI:6012067 |
| mmoZ | *Methylococcus capsulatus* (Bath) | GI:7770067 |
| mmoB | *Methylococcus capsulatus* (Bath) | GI:7770068 |
| mmoC | *Methylococcus capsulatus* (Bath) | GI:7770065 |
| orfY | *Methylococcus capsulatus* (Bath) | GI:6119486 |
| mmoR | *Methylosinus trichosporium* OB3b | GI:28070884 |
| mmoG | *Methylosinus trichosporium* OB3b | GI:28070885 |
| mmoX | *Methylosinus trichosporium* OB3b | GI:5102756 |
| mmoY | *Methylosinus trichosporium* OB3b | GI:44615 |
| mmoB | *Methylosinus trichosporium* OB3b | GI:44616 |
| mmoZ | *Methylosinus trichosporium* OB3b | GI:44617 |
| mmoD | *Methylosinus trichosporium* OB3b | GI:28070886 |
| mmoC | *Methylosinus trichosporium* OB3b | GI:5102757 |

MMOs may be tested from the organisms set forth in Table 3, whose full genome sequences are in various stages of preparation. The sequences code for either sMMO or pMMO complexes. These genes may then either amplified from genomic DNA using PCR, or else codon optimized and synthesized by a company such as DNA 2.0.

TABLE 3

| Strain | GenBank accession/JGI ID |
|---|---|
| *Methylocapsa acidiphila* B2 | ABLP0100000 |
| *Methylosinus trichosporium* OB3b | ADVE00000000 |
| *Methylococcus capsulatus* BATH | AE017282.2 |
| *Methylobacter tundripaludum*SV96 | AEGW00000000 |
| *Methylocystis* sp. strain Rockwell | AEVM00000000 |
| *Methylocystis parvus* OBBP | AJTV00000000 |
| *Methylococcus capsulatus*TexasATCC19069 | AMCE00000000 |
| *Methylomicrobiumburyatense* 5G | AOTL00000000 |
| *Methylomonas*MK1 | AQOV00000000 |
| *Methylobacter* sp. BBA5 (synonym UW 659-2-H10) | AQVZ01000000 |
| *Methylovulum miyakonense* HT12$^T$ | AQZU01000000 |
| *Methylosinus* sp. LW4 | ARAB00000000 |
| *Verrucomicrobium*sp. 3C | ARAS01000000 |
| *Methylocystis rosea* SV97$^T$ | ARCT0100000 |
| *Methylosarcina fibrata* AML-C10$^T$ | ARCU01000000 |
| *Methylobacter marinus* A45 | ARVS00000000 |
| *Methyloferula stellata* AR4$^T$ | ARWA01000000 |
| *Methylohalobius crimeensis* 10Ki$^T$ | ATXB01000000 |
| *Methylobacter luteus* (synonym*M. bovis*) IMV-B-3098$^T$ | ATYJ01000000 |
| *Methylacidiphilum fumariolicum* SolV | CAHT00000000 |
| *Methylomicrobiumalbum* BG8 | CM001475 |
| *Methylacidiphilum infernorum* V4 | CP000975.1 |
| *Methylomonas methanica* MC09 | NC_015572 |
| *Methylomicrobium alcaliphilum* 20Z | NC_016112 |
| *Methylocystis* sp. SC2 | NC_018485 |
| *Methylomonas*11b | PRJNA157071 |
| *Methylocaldum szegediense* O-12 | SRX030733 |

Additional full genome sequences will likely become public, and a similar analysis is applied to any the following genomes, or any other sequence that becomes available for a methanotroph.

TABLE 4

| Strain |
|---|
| *Methylacidiphilum kamchatkense* Kam1 |
| *Methylosinus* sp. LW8 |
| *Methylosinus* sp. LW3 |
| *Methylosinus* sp. PW1 |
| *Methylosinus sporium* sp. 5$^T$ |
| *Methylocystis* sp. LW5 |
| *Methylocapsa aurea* KYG$^T$ |

TABLE 4-continued

| Strain |
|---|
| *Methylomonas* LW13 |
| *Methylosarcina lacus* LW14 |
| *Methylobacter whittenburyi* (synonym *M. vinelandii*) ACM 3586$^T$ |
| *Methylobacter* BB5 |
| *Methylobacter* 31-32 |
| *Methylococaceae* 12 |
| *Methylomicrobium pelagicum* sp. D100#4 |
| *Methylomicrobium agile* |
| *Methylomonas* sp. LWB |
| *Methylomarinum vadi* |
| *Methylocaldum*sp. 175 |
| *Verrucomicrobium*sp. LP2A |

Example 5. Identifying Genetic Elements that Improve MMO Function

This example describes the construction of a genetically engineered host cell wherein the expression of exogenous genes coding for proteins or RNAs of unknown function in the engineered host cell results in an engineered cell improved for growth on methane.

Complementation libraries may be searched for protein partners or chaperones that are missing from the host strain, and whose expression increases the growth rate on methane. Here, libraries will be constructed by cloning plasmids containing random genomic DNA fragments from a natural methanotroph. Genomic DNA will be isolated from one or more methanotrophs, digested or sheared into fragments, and cloned into a plasmid suitable to the host strain. In some cases, for expression in a yeast host strain, a yeast artificial chromosome may be appropriate. In some cases, for expression in a bacterial host strain, a cosmid, or a bacterial artificial chromosome may be appropriate. In some cases, the digested methanotroph genomic DNA is linked to a selective marker, and integrated directly into a host cell chromosome. Improvements in growth rate or product formation may be measured, as described herein. Genome-scale analysis may reduce the size of such libraries, and genomic intersection techniques may identify genes common to MMO-expressing organisms and absent in the engineered host (M G KALYUZHNAYA ET AL., FUNCTIONAL METAGENOMICS OF METHYLOTROPHS, 495 METHODS IN ENZYMOLOGY 81-98, 2011).

Loss-of-function strain libraries may be used to identify genes essential for oxidation of methane to methanol. Here, a strain collection with random genetic changes ("a library") may be generated in a natural methanotroph, and the reduction (or loss) of its ability to grow on methane is used to identify key genes. These genes may then be expressed in the engineered host cell and tested for improvements in host cell growth using methane as the carbon source.

One example of this type of library is a transposon library. A large library may be generated in a natural methanotroph. This library would be plated onto methanol-containing agar plates and then replica-plated onto agar plates without methanol, but grown in the presence of gaseous methane. Mutants with diminished MMO activity will be able to grow on methanol, but will have decreased growth rate on methane. Mutations can be identified using arbitrarily primed PCR methods. This method identifies genetic elements that are tested in our synthetic methanotrophs for growth improvement in a methane-fed fermentation. This example of transposon mutagenesis is exemplary and not meant to be limiting. The method of screening a mutated methanotroph applies equally well to other methods of mutagenesis, such as, but not limited to, chemical mutagenesis, ultraviolet-light-induced mutagenesis, targeted mutagenesis, and others.

Example 6. Synthetic Methanotrophic *Pichia pastoris*-Derived Strain Capable of Producing Malate This example describes a non-naturally occurring microorganism capable of consuming methane and producing malate.

The strains of *Pichia pastoris* described above in Examples 1 and 4 may be combined to generate a strain capable of methane utilization and malate production. Methods to combine genetic elements from two strains into one strain are well understood Sherman. One method to combine two *Pichia pastoris* strains is via mating and sporulation. This assumes that the genetic elements are on separate chromosomes or are sufficiently separated on the chromosome to allow for a crossover event. If the genetic elements are linked to selectable markers, then selection after sporulation can simplify the identification of desirable clones.

A second standard method is to amplify by PCR the genetic elements from one strain and transform them into a recipient strain. The genetic elements are transferred one at a time or multiple elements at the same time, depending on the selectable markers.

In a third standard method, the genetic elements reside on one or more episomal plasmids or artificial chromosomes or completely synthetic chromosomes and are purified and transformed into a recipient strain (N Annaluru et al., *Total synthesis of a functional designer eukaryotic chromosome*, 344 SCIENCE (NEW YORK, N.Y.) 55-8, 2014). Additional methods combine these methods and depend on the exact genetic context of the nucleic acids that enable the invention.

Methods to culture a synthetic methanotrophic derivative of *P. pastoris* are straightforward for one skilled in the art. Briefly, a minimal media can be prepared with all components except a carbon source. The minimal media may contain bicarbonate. Strains are grown in rich media and then inoculated into flasks, stoppered bottles, or bioreactors. Methane, carbon dioxide, air, and/or oxygen are sparged or added to the headspace above the liquid. Typically, flasks and bottles are shaken and bioreactors are stirred. All cultures are temperature-controlled at a temperature that is optimal for growth or production. After the cultures have fermented for sufficient time to produce malate, the culture is centrifuged and samples of the supernatant are analyzed by HPLC in order to quantify the concentration of malate.

Example 7. Co-Culturing Two or More Microorganisms in Order to Generate a Chemical Product from Methane This example provides a method for co-culturing two or more microorganisms in order to generate a product wherein one of the microorganisms can consume methane and produce an intermediate chemical, such as, but not limited to, methanol or formaldehyde, and another of the microorganisms can consume said intermediate chemical and generate a chemical product.

As described above, *Pichia pastoris* and other methylotrophic yeasts can consume methanol as a sole carbon and energy source. Metabolic engineering *P. pastoris* to produce a chemical, such as in Example 1, generates a strain capable of converting methanol into the chemical. In this example, the methanol may be derived from oxidation of methane by a methanotrophic microorganism. Some methanotrophic bacteria, for example, have been shown to produce methanol at high rates under certain culturing conditions (J Han et al., *Partial oxidative conversion of methane to methanol through selective inhibition of methanol dehydrogenase in methanotrophic consortium from landfill cover soil*, 171 APPLIED BIOCHEMISTRY AND BIOTECHNOLOGY 1487-99, 2013); (H G Kim et al., *Optimization of lab scale methanol production by Methylosinus trichosporium OB3b*, BIOTECHNOLOGY AND BIOPROCESS ENGINEERING, 2010); (C Duan et al., *High-rate conversion of methane to methanol by Methylosinus trichosporium OB3b*, 102 BIORESOURCE TECHNOLOGY 7349-53, 2011).

In one embodiment, the methanotrophic bacteria will be co-cultured with an engineered *P. pastoris* strain under culturing conditions to enable the methanotrophic bacteria to convert methane into methanol, which can be consumed by the *P. pastoris* strain, which can produce a molecule of interest, such as, but not limited to, malate, succinate, or fumarate.

In another embodiment, the methanotrophic bacteria can be co-cultured with an engineered *P. pastoris* strain under culturing conditions to enable the methanotrophic bacteria to convert methane into formaldehyde, which is consumed by the *P. pastoris* strain, which produces a molecule of interest, such as, but not limited to, malate, succinate, or fumarate.

In another embodiment, the methanotrophic bacteria have been genetically modified to increase production of methanol and/or formaldehyde from methane under certain culturing conditions. Such modifications may result in, but are not limited to, any of the following: upregulation of the genes involved in the MMO complex, altered transcription factor expression or activation of the MMO genes, stabilization of the mRNA transcript corresponding to a component of the MMO complex, increased protein translation of any MMO component or related protein (such as a protein folding chaperone or catalase), increased cofactor availability, stabilization of the proteins involved in the MMO complex or related proteins, downregulation of genes and enzymes that consume the intermediate chemical (methanol or formaldehyde or other), mutations in relevant genes in the MMO complex or related proteins. The genetic changes may be targeted or randomly introduced.

In any of the described examples above, the cultures may be grown, together or separately, under certain conditions (for example, that may be favorable for growth) and switched to a second set of conditions that may be optimal for production of said molecule from methane. Some examples of conditions that may be adjusted are, but are not limited to, the following: dissolved oxygen, carbon dioxide, or methane concentration and flow rate, salt concentration, trace minerals concentrations, trace vitamins concentrations, copper or iron concentration, nitrogen and phosphate availability, temperature, pressure, stirring rate, and shaking rate.

All references cited herein are incorporated by reference as if each had been individually incorporated by reference in its entirety. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A synthetic microorganism of *Escherichia coli* comprising one or more genetic modifications encoding a soluble methane monooxygenase that allows said *Escherichia coli* to oxidize methane, wherein the one or more genetic modifications comprises the genes mmoB, mmoC, mmoX, mmoY, and mmoZ and the one or more genetic modifications additionally comprises one or more exogenous polynucleotides encoding exogenous expression of one or more protein-folding chaperones.

2. The synthetic microorganism of claim 1, wherein said one or more genetic modifications further comprise one or more exogenous polynucleotides additionally encoding accessory proteins and/or additionally encoding one or more helper proteins.

3. The synthetic microorgansim of claim 2, wherein the one or more exogenous polynucleotides are expressed from one or more chromosomal locations and/or from one or more plasmid locations.

4. A method for producing methanol, comprising culturing the synthetic microorganism of claim 1 under suitable culture conditions and for a sufficient period of time to produce said methanol.

5. The method of claim 4, wherein the sufficient period of time comprises at least 5 minutes.

* * * * *